(12) United States Patent
Albert et al.

(10) Patent No.: US 7,108,866 B1
(45) Date of Patent: Sep. 19, 2006

(54) CHRONOTHERAPEUTIC DILTIAZEM FORMULATIONS AND THE ADMINISTRATION THEREOF

(75) Inventors: Kenneth Stephen Albert, Mt. Kisco, NY (US); Paul José Maes, Oakville (CA)

(73) Assignee: Biovall Laboratories International SRL, St. Michael (BB)

( * ) Notice: Subject to any disclaimer, the term of this patent is extended or adjusted under 35 U.S.C. 154(b) by 0 days.

(21) Appl. No.: 09/567,451

(22) Filed: May 8, 2000

Related U.S. Application Data

(63) Continuation-in-part of application No. 09/465,338, filed on Dec. 17, 1999, now abandoned.

(30) Foreign Application Priority Data

Dec. 10, 1999 (CA) .................................. 2292247
May 4, 2000 (CA) .................................. 2307547

(51) Int. Cl.
*A61K 9/22* (2006.01)
*A61K 9/26* (2006.01)
*A61K 9/48* (2006.01)
*A61K 9/50* (2006.01)
*A61K 9/52* (2006.01)

(52) U.S. Cl. ...................... 424/490; 424/452; 424/457; 424/458; 424/465; 424/468; 424/469

(58) Field of Classification Search ............... 424/457, 424/468, 451, 452, 463, 464, 465, 471, 474, 424/489, 490, 493
See application file for complete search history.

(56) References Cited

U.S. PATENT DOCUMENTS 4,263,273 A    4/1981   Appelgren et al. ........... 424/21
4,327,725 A    5/1982   Cortese et al. .............. 128/260
4,600,645 A    7/1986   Ghebre-Sellassie et al. 428/403
4,612,008 A    9/1986   Wong et al. ................ 604/892
4,623,588 A    11/1986  Nuwayser et al. ..... 428/402.24
4,628,047 A    12/1986  Sakurai et al.

(Continued)

FOREIGN PATENT DOCUMENTS

EP    0 149 920 A2   12/1984

(Continued)

OTHER PUBLICATIONS

Klokkers-Bethke, K. et al., "Development of a multiple unit drug delivery system for positioned release in the gastrointestinal tract", *Journal of Controlled Release*, 15 (1991) 105-112.

(Continued)

*Primary Examiner*—S. Tran
(74) *Attorney, Agent, or Firm*—Hunton & Williams; Robin L. Teskin

(57) ABSTRACT

A controlled-release Galenical preparation of pharmaceutically acceptable Diltiazem including the pharmaceutically acceptable salts thereof, suitable for evening dosing every 24 hours containing from about 120 mg to about 540 mg or more (as desired) of the form of Diltiazem associated with excipients to provide controlled (sustained) release of the form of Diltiazem for providing a $C_{max}$ of Diltiazem in the blood at between about 10 hours and about 15 hours after administration, the preparation comprising the form of Diltiazem in oral sustained-release dosage form in which the Diltiazem is adapted to be released after administration over a prolonged period of time and exhibits when given to humans
(i) a higher bioavailability when given at night compared to when given in the morning without food according to FDA guidelines or criteria and
(ii) bioequivalence when given in the morning with and without food according to the same FDA guidelines or criteria.

88 Claims, 15 Drawing Sheets

U.S. PATENT DOCUMENTS

| | | | |
|---|---|---|---|
| 4,696,924 A | 9/1987 | Marcoux | 514/211 |
| 4,705,695 A | 11/1987 | Lehmann et al. | 427/3 |
| 4,721,619 A | 1/1988 | Panoz et al. | 424/459 |
| 4,753,802 A | 6/1988 | Stephens et al. | 424/467 |
| 4,783,337 A | 11/1988 | Wong et al. | 424/468 |
| 4,784,858 A | 11/1988 | Ventouras | 424/468 |
| 4,792,452 A | 12/1988 | Howard et al. | 424/475 |
| 4,808,413 A | 2/1989 | Joshi et al. | 424/458 |
| 4,824,678 A | 4/1989 | Lindahl et al. | 424/473 |
| 4,832,958 A | 5/1989 | Baudier et al. | 424/473 |
| 4,839,177 A | 6/1989 | Colombo et al. | 424/482 |
| 4,859,469 A | 8/1989 | Baudier et al. | 424/462 |
| 4,859,470 A | 8/1989 | Guittard et al. | 424/473 |
| 4,880,631 A | 11/1989 | Haslam et al. | 424/424 |
| 4,891,230 A | 1/1990 | Geoghegan et al. | 424/461 |
| 4,894,240 A | 1/1990 | Geoghegan et al. | 424/497 |
| 4,917,899 A | 4/1990 | Geoghegan et al. | 424/461 |
| 4,938,967 A | 7/1990 | Newton et al. | 424/458 |
| 4,940,588 A | 7/1990 | Sparks et al. | 424/490 |
| 4,952,402 A | 8/1990 | Sparks et al. | 424/419 |
| 4,960,596 A | 10/1990 | Debregeas et al. | 424/458 |
| 4,966,769 A | 10/1990 | Guittard et al. | 424/473 |
| 5,000,962 A | 3/1991 | Sangekar et al. | 424/482 |
| 5,002,776 A | 3/1991 | Geoghegan et al. | 424/497 |
| 5,004,614 A | 4/1991 | Staniforth | 424/466 |
| 5,008,114 A | 4/1991 | Lovrecich | 424/484 |
| 5,051,262 A | 9/1991 | Panoz et al. | 424/468 |
| 5,055,306 A * | 10/1991 | Barry et al. | 424/482 |
| 5,082,668 A | 1/1992 | Wong et al. | 424/473 |
| 5,112,621 A | 5/1992 | Stevens et al. | 424/497 |
| 5,149,542 A | 9/1992 | Valducci | 424/493 |
| 5,156,850 A | 10/1992 | Wong et al. | 424/473 |
| 5,160,744 A | 11/1992 | Jao et al. | 424/473 |
| 5,175,003 A | 12/1992 | Goldman | 424/484 |
| 5,178,867 A | 1/1993 | Guittard et al. | 424/473 |
| 5,190,765 A | 3/1993 | Jao et al. | 424/473 |
| 5,219,621 A | 6/1993 | Geoghegan et al. | 424/462 |
| 5,229,135 A | 7/1993 | Philippon et al. | 424/494 |
| 5,252,338 A | 10/1993 | Jao et al. | 424/473 |
| 5,260,068 A | 11/1993 | Chen | 424/451 |
| 5,260,069 A | 11/1993 | Chen | 424/451 |
| 5,275,824 A | 1/1994 | Carli et al. | 424/490 |
| 5,286,497 A * | 2/1994 | Hendrickson et al. | 424/490 |
| 5,288,505 A | 2/1994 | Deboeck et al. | 424/497 |
| 5,326,571 A | 7/1994 | Wright et al. | 424/473 |
| 5,330,761 A | 7/1994 | Baichwal | 424/469 |
| 5,336,504 A | 8/1994 | Geoghegan et al. | 424/462 |
| 5,344,657 A | 9/1994 | Desmolin | 424/458 |
| 5,354,556 A | 10/1994 | Sparks et al. | 424/419 |
| 5,364,620 A | 11/1994 | Geoghegan et al. | 424/497 |
| 5,419,917 A | 5/1995 | Chen et al. | 429/469 |
| 5,439,689 A | 8/1995 | Hendrickson et al. | 424/490 |
| 5,445,829 A | 8/1995 | Paradissis et al. | 424/480 |
| 5,449,521 A | 9/1995 | Lovrecich | 424/489 |
| 5,455,046 A | 10/1995 | Baichwal | 424/457 |
| 5,458,887 A | 10/1995 | Chen et al. | 424/464 |
| 5,458,888 A | 10/1995 | Chen | 424/464 |
| 5,464,633 A | 11/1995 | Conte et al. | 424/480 |
| 5,470,584 A | 11/1995 | Hendrickson et al. | 424/490 |
| 5,472,708 A | 12/1995 | Chen | 424/451 |
| 5,472,711 A | 12/1995 | Baichwal | 424/468 |
| 5,478,574 A | 12/1995 | Baichwal et al. | 424/485 |
| 5,508,040 A | 4/1996 | Chen | 424/451 |
| 5,512,297 A | 4/1996 | Baichwal | 424/451 |
| 5,529,790 A | 6/1996 | Eichel et al. | 424/480 |
| 5,529,791 A | 6/1996 | Deboeck et al. | 424/494 |
| 5,554,387 A | 9/1996 | Baichwal | 424/488 |
| 5,558,879 A | 9/1996 | Chen et al. | 424/480 |
| 5,567,441 A | 10/1996 | Chen | 424/494 |
| 5,601,845 A | 2/1997 | Buxton et al. | 424/495 |
| 5,616,345 A | 4/1997 | Geoghegan et al. | 424/497 |
| 5,622,716 A | 4/1997 | Barth | 424/461 |
| 5,626,860 A | 5/1997 | Cincotta et al. | 424/423 |
| 5,654,005 A | 8/1997 | Chen et al. | 424/480 |
| 5,662,933 A | 9/1997 | Baichwal et al. | 424/457 |
| 5,667,801 A | 9/1997 | Baichwal | 424/457 |
| 5,670,168 A | 9/1997 | Baichwal et al. | 424/464 |
| 5,670,172 A | 9/1997 | Buxton et al. | 424/495 |
| 5,681,583 A | 10/1997 | Conte et al. | 424/472 |
| 5,688,794 A | 11/1997 | Meier et al. | 514/250 |
| 5,716,933 A | 2/1998 | Meier et al. | 514/12 |
| 5,716,962 A | 2/1998 | Cincotta et al. | 514/288 |
| 5,736,159 A | 4/1998 | Chen et al. | 424/480 |
| 5,756,513 A | 5/1998 | Cincotta et al. | 514/288 |
| 5,773,025 A | 6/1998 | Baichwal | 424/458 |
| 5,785,994 A | 7/1998 | Wong et al. | 424/473 |
| RE35,903 E | 9/1998 | Debregaes et al. | 424/458 |
| 5,830,503 A | 11/1998 | Chen | 424/480 |
| 5,834,023 A | 11/1998 | Chen | 424/497 |
| 5,834,024 A | 11/1998 | Heinicke et al. | 424/497 |
| 5,837,379 A | 11/1998 | Chen et al. | 424/465 |
| 5,840,329 A | 11/1998 | Bai | 424/458 |
| 5,843,347 A | 12/1998 | Nguyen et al. | 264/9 |
| 5,846,563 A | 12/1998 | Baichwal | 424/457 |
| 5,851,555 A | 12/1998 | Sanghvi et al. | 424/464 |
| 5,869,097 A | 2/1999 | Wong et al. | 424/473 |
| 5,914,134 A | 6/1999 | Sharma | 424/497 |
| 5,916,595 A | 6/1999 | Chen et al. | 424/480 |
| 5,922,352 A | 7/1999 | Chen et al. | 424/465 |
| 5,945,125 A | 8/1999 | Kim | 424/473 |
| 5,958,456 A | 9/1999 | Baichwal et al. | 424/489 |
| 6,004,582 A | 12/1999 | Faour et al. | 424/473 |
| 6,022,562 A | 2/2000 | Autant et al. | 424/489 |
| 6,033,687 A | 3/2000 | Heinicke et al. | 424/497 |

FOREIGN PATENT DOCUMENTS

| | | |
|---|---|---|
| EP | 0 263 083 A1 | 9/1987 |
| EP | 0 282 698 A | 1/1988 |
| EP | 0 309 051 A1 | 9/1988 |
| EP | 0 320 097 A1 | 10/1988 |
| EP | 0 856 313 A1 | 10/1988 |
| EP | 0 315 414 A1 | 11/1988 |
| EP | 0 318 398 A1 | 11/1988 |
| EP | 0 322 277 A1 | 12/1988 |
| EP | 0 340 105 A1 | 4/1989 |
| EP | 0 342 106 A1 | 5/1989 |
| EP | 0 373 417 A1 | 11/1989 |
| EP | 0 605 174 A | 12/1993 |
| EP | 0 527 637 B1 | 4/1998 |
| EP | 0856313 * | 8/1998 |
| EP | 0 682 945 B1 | 6/1999 |
| EP | 0 591 424 B1 | 9/1999 |
| WO | WO 90/06107 | 6/1990 |
| WO | WO 91/01722 | 2/1991 |
| WO | WO 93/0093 | 1/1993 |
| WO | WO 9300093 A1 * | 1/1993 |
| WO | WO 93/09767 | 5/1993 |
| WO | WO 96/29992 | 10/1996 |
| WO | WO 97/23219 | 7/1997 |
| WO | WO 97/48386 | 12/1997 |
| WO | WO 98/32424 | 7/1998 |
| WO | WO 98/33488 | 8/1998 |
| WO | WO 98/33489 | 8/1998 |

OTHER PUBLICATIONS

Deedwanian, C. et al., Effect of Morning Versus Evening Dosing of Diltiazem on Myocardial Ischemia Detected by Ambulatory Electrocardiographic Monitoring in Chronic Stable Angio Pectoris, Pra Kash, *The American Journal of Cardiology*, vol. 80, Aug. 15, 1997, p. 421-425.

Kelly, J.G. et al., Pharmacokinetic Properties and Antihypertensive Efficacy of Once-Daily Diltiazem, *Journal of Cardio-Vascular Pharmacology*, 17:6:957-963, (1991).

Kohno, I. et al., Administration Time—Dependent Effects of Diltiazem on The 24-Hour Blood Pressure Profile of Essential Hypertension Patients, *Chronobiology International*, 14(1), 71-84, (1997).

Leeuwenkamp, O.R. et al, A comparative study of the steady-state pharmacokinetics of immediate-release and controlled-release diltiazem tablets, *Eur. J. Clin. Pharmacol*, (1994) 46:243-247.

Thiffault, J. et al., The Influence of Time Administration on the Pharmacokinetics of a Once A Day Diltiazem Formulation: Morning Against Bedtime, *Biopharmaceutics & Drug Disposition*, vol. 17, 107-115 (1996).

Zahirul, M. et al., Recent Trends and Progress in Substained or Controlled Oral Delivery of Some Water Soluble Drugs: Morphine Salts, Diltiazem and Captopril, *Drug Development and Industrial Pharmacy*, US, New York, NY, vol. 21, No. 9, Jan. 1, 1995, pp. 1037-1070.

\* cited by examiner

Diltiazem AUCt PK Summary

Formulation According to Embodiment of Invention

| Subject | Morning Fasting AUCt | Log AUCt | Morning Fed AUCt | Log AUCt | Night Dosing AUCt | Log AUCt | Morning Fed/Fast Ratio | Night/Morning Ratio |
|---|---|---|---|---|---|---|---|---|
| 2 | 1730.75 | 7.46 | 2647.15 | 7.88 | 1987.11 | 7.59 | 1.53 | 1.15 |
| 3 | 2712.98 | 7.91 | 2336.67 | 7.76 | 3249.94 | 8.09 | 0.86 | 1.20 |
| 4 | 2688.34 | 7.90 | 1907.61 | 7.55 | 2892.21 | 7.97 | 0.71 | 1.08 |
| 5 | 4192.37 | 8.34 | 4108.85 | 8.32 | 4702.33 | 8.46 | 0.98 | 1.12 |
| 6 | 3074.51 | 8.03 | 2887.98 | 7.97 | 3900.06 | 8.27 | 0.94 | 1.27 |
| 7 | 1629.81 | 7.40 | 1847.56 | 7.52 | 2723.36 | 7.91 | 1.13 | 1.67 |
| 8 | 941.10 | 6.85 | 1970.97 | 7.59 | 1835.11 | 7.51 | 2.09 | 1.95 |
| 9 | 3144.13 | 8.05 | 3462.59 | 8.15 | 2923.86 | 7.98 | 1.10 | 0.93 |
| 10 | 2074.94 | 7.64 | 2997.45 | 8.01 | 4028.83 | 8.30 | 1.44 | 1.94 |
| 11 | 3653.96 | 8.20 | 2771.53 | 7.93 | 3464.72 | 8.15 | 0.76 | 0.95 |
| 12 | 2684.22 | 7.90 | 3790.43 | 8.24 | 3141.47 | 8.05 | 1.41 | 1.17 |
| 13 | 3352.69 | 8.12 | 3751.95 | 8.23 | 3708.83 | 8.22 | 1.12 | 1.11 |
| 14 | 2988.61 | 8.00 | 3665.60 | 8.21 | 3141.05 | 8.05 | 1.23 | 1.05 |
| 15 | 6796.97 | 8.82 | 8204.22 | 9.01 | 7578.33 | 8.93 | 1.21 | 1.11 |
| 16 | 2873.70 | 7.96 | 4644.79 | 8.44 | 4192.09 | 8.34 | 1.62 | 1.46 |
| 17 | 4468.33 | 8.40 | 4222.55 | 8.35 | 3762.50 | 8.23 | 0.94 | 0.84 |
| 18 | 5654.29 | 8.64 | 5635.72 | 8.64 | 7159.38 | 8.88 | 1.00 | 1.27 |
| 19 | 4944.07 | 8.51 | 5107.44 | 8.54 | 4812.20 | 8.48 | 1.03 | 0.97 |
| 20 | 2986.73 | 8.00 | 2988.34 | 8.00 | 2791.23 | 7.93 | 1.00 | 0.93 |
| 21 | 2908.88 | 7.98 | 3314.12 | 8.11 | 4389.98 | 8.39 | 1.14 | 1.51 |
| 22 | 4270.43 | 8.36 | 3790.06 | 8.24 | 3631.01 | 8.20 | 0.89 | 0.85 |
| 23 | 6150.18 | 8.72 | 6092.56 | 8.71 | 7478.22 | 8.92 | 0.99 | 1.22 |
| 25 | 2926.46 | 7.98 | 5633.64 | 8.64 | 4839.10 | 8.48 | 1.93 | 1.65 |
| 26 | 3928.61 | 8.28 | 4614.43 | 8.44 | 4359.77 | 8.38 | 1.17 | 1.11 |
| 27 | 3637.94 | 8.20 | 4587.48 | 8.43 | 4063.15 | 8.31 | 1.26 | 1.12 |
| 28 | 4177.76 | 8.34 | 4945.31 | 8.51 | 6689.14 | 8.81 | 1.18 | 1.60 |
| 29 | 3609.69 | 8.19 | 2720.67 | 7.91 | 2163.20 | 7.68 | 0.75 | 0.60 |
| 30 | 4483.17 | 8.41 | 5222.54 | 8.56 | 5587.50 | 8.63 | 1.16 | 1.25 |
| 32 | 4058.04 | 8.31 | 3531.47 | 8.17 | 3082.87 | 8.03 | 0.87 | 0.76 |
| Mean | 3542.88 | 8.10 | 3910.40 | 8.21 | 4078.57 | 8.25 | 1.15 | 1.20 |
| SD | 1304.23 | 0.41 | 1431.24 | 0.36 | 1554.69 | 0.37 | 0.33 | 0.33 |
| CV | 36.81 | 5.08 | 36.60 | 4.43 | 38.12 | 4.46 | 28.23 | 27.33 |
| Median | 3352.69 | 8.12 | 3751.95 | 8.23 | 3762.50 | 8.23 | 1.12 | 1.12 |
| Geo Mean | 3292.83 | 8.09 | 3671.24 | 8.20 | 3818.30 | 8.24 | 1.11 | 1.16 |

Fed/Fasting Ratio (Morning Dosing)

| | | |
|---|---|---|
| Ratio of Means | 1.10 | # |
| Ratio of Geo Means | 1.11 | # |
| Avg of Individual Ratios | 1.15 | # |

Night/Morning Ratio

| | |
|---|---|
| Ratio of Means | 1.15 |
| Ratio of Geo Means | 1.16 |
| Avg of Individual Ratios | 1.20 |

Fig. 9A

Diltiazem Cmax PK Summary

Formulation According to Embodiment of Invention

| Subject | Morning Fasting Tmax | Morning Fasting Cmax | Morning Fasting Log Cmax | Morning Fed Tmax | Morning Fed Cmax | Morning Fed Log Cmax | Night Dosing Tmax | Night Dosing Cmax | Night Dosing Log Cmax | Morning Fed/Fast Ratio | Night/Morning Ratio |
|---|---|---|---|---|---|---|---|---|---|---|---|
| 2 | 10.0 | 98.63 | 4.59 | 10.0 | 187.71 | 5.23 | 13.0 | 143.84 | 4.97 | 1.90 | 1.46 |
| 3 | 13.0 | 136.18 | 4.91 | 11.0 | 123.04 | 4.81 | 10.0 | 246.57 | 5.51 | 0.90 | 1.81 |
| 4 | 15.0 | 133.23 | 4.89 | 10.0 | 118.68 | 4.78 | 10.0 | 191.44 | 5.25 | 0.89 | 1.44 |
| 5 | 8.0 | 222.52 | 5.41 | 8.0 | 195.68 | 5.28 | 12.0 | 254.98 | 5.54 | 0.88 | 1.15 |
| 6 | 12.0 | 150.95 | 5.02 | 8.0 | 164.11 | 5.10 | 16.0 | 179.67 | 5.19 | 1.09 | 1.19 |
| 7 | 10.0 | 90.66 | 4.51 | 14.0 | 121.64 | 4.80 | 12.0 | 179.67 | 5.19 | 1.34 | 1.98 |
| 8 | 8.0 | 65.66 | 4.18 | 11.0 | 119.30 | 4.78 | 11.0 | 133.35 | 4.89 | 1.82 | 2.03 |
| 9 | 13.0 | 155.46 | 5.05 | 6.0 | 292.70 | 5.68 | 12.0 | 175.62 | 5.17 | 1.88 | 1.13 |
| 10 | 8.0 | 95.45 | 4.56 | 6.0 | 166.91 | 5.12 | 13.0 | 196.94 | 5.28 | 1.75 | 2.06 |
| 11 | 14.0 | 212.41 | 5.36 | 11.0 | 154.64 | 5.04 | 14.0 | 183.66 | 5.21 | 0.73 | 0.86 |
| 12 | 10.0 | 117.75 | 4.77 | 10.0 | 201.43 | 5.31 | 11.0 | 174.85 | 5.16 | 1.71 | 1.49 |
| 13 | 14.0 | 149.90 | 5.01 | 13.0 | 188.51 | 5.24 | 10.0 | 208.78 | 5.34 | 1.26 | 1.39 |
| 14 | 13.0 | 139.54 | 4.94 | 6.0 | 205.35 | 5.32 | 13.0 | 187.32 | 5.23 | 1.47 | 1.34 |
| 15 | 16.0 | 266.48 | 5.59 | 15.0 | 330.93 | 5.80 | 13.0 | 450.34 | 6.11 | 1.24 | 1.69 |
| 16 | 13.0 | 134.55 | 4.90 | 8.0 | 281.74 | 5.64 | 10.0 | 236.10 | 5.46 | 2.09 | 1.75 |
| 17 | 12.0 | 224.65 | 5.41 | 10.0 | 244.82 | 5.50 | 14.0 | 203.51 | 5.32 | 1.09 | 0.91 |
| 18 | 14.0 | 281.88 | 5.64 | 8.0 | 308.25 | 5.73 | 13.0 | 479.11 | 6.17 | 1.09 | 1.70 |
| 19 | 15.0 | 227.89 | 5.43 | 11.0 | 262.82 | 5.57 | 13.0 | 231.49 | 5.44 | 1.15 | 1.02 |
| 20 | 14.0 | 137.54 | 4.92 | 10.0 | 175.76 | 6.17 | 10.0 | 173.93 | 5.16 | 1.28 | 1.26 |
| 21 | 13.0 | 164.75 | 5.10 | 13.0 | 197.63 | 5.29 | 13.0 | 301.72 | 5.71 | 1.20 | 1.83 |
| 22 | 16.0 | 182.52 | 5.21 | 11.0 | 207.19 | 5.33 | 10.0 | 247.08 | 5.51 | 1.14 | 1.35 |
| 23 | 18.0 | 269.97 | 5.60 | 10.0 | 340.21 | 5.83 | 10.0 | 500.82 | 6.22 | 1.26 | 1.86 |
| 25 | 10.0 | 166.06 | 5.11 | 8.0 | 322.55 | 5.78 | 10.0 | 263.27 | 5.57 | 1.94 | 1.59 |
| 26 | 13.0 | 208.19 | 5.34 | 10.0 | 237.50 | 5.47 | 10.0 | 235.12 | 5.46 | 1.14 | 1.13 |
| 27 | 10.0 | 162.47 | 5.09 | 8.0 | 255.85 | 5.54 | 10.0 | 170.18 | 5.14 | 1.57 | 1.05 |
| 28 | 13.0 | 218.59 | 5.39 | 11.0 | 238.10 | 5.46 | 11.0 | 384.02 | 5.95 | 1.08 | 1.76 |
| 29 | 13.0 | 215.15 | 5.37 | 13.0 | 160.73 | 5.08 | 12.0 | 129.94 | 4.87 | 0.75 | 0.60 |
| 30 | 14.0 | 242.66 | 5.49 | 12.0 | 244.58 | 5.50 | 10.0 | 336.64 | 5.82 | 1.01 | 1.39 |
| 32 | 12.0 | 303.43 | 5.72 | 15.0 | 204.09 | 5.32 | 11.0 | 231.33 | 5.44 | 0.67 | 0.76 |
| Mean | 12.6 | 178.45 | 5.12 | 10.2 | 215.53 | 5.33 | 11.6 | 242.46 | 5.42 | 1.29 | 1.41 |
| SD | 2.5 | 61.85 | 0.37 | 2.5 | 64.85 | 0.31 | 1.6 | 98.98 | 0.36 | 0.40 | 0.39 |
| CV | 19.8 | 34.66 | 7.32 | 24.3 | 30.09 | 5.83 | 14.1 | 40.82 | 6.58 | 30.69 | 27.83 |
| Median | 13.0 | 164.75 | 5.10 | 10.0 | 204.09 | 5.32 | 11.0 | 208.78 | 5.34 | 1.20 | 1.39 |
| Geo Mean | 12.3 | 157.47 | 5.11 | 9.9 | 206.00 | 5.32 | 11.5 | 226.83 | 5.41 | 1.23 | 1.35 |

Fed/Fasting Ratio (Morning Dosing)

Ratio of Means 1.21
Ratio of Geo Means 1.23
Avg of Individual Ratios 1.29

Night/Morning Ratio

Ratio of Means 1.36
Ratio of Geo Means 1.35
Avg of Individual Ratios 1.41

Fig. 9B

PK Summary (N=30)

Diltiazem PK

Open Capsule Sprinkled on Applesauce / Capsule Intact

<u>AUCt</u>

| | |
|---|---|
| Ratio of Means % | 94.16 |
| Ratio of Geo Means % | 93.98 |
| Avg of Individual Ratios % | 96.03 |
| 90% C.I. | 88%-99% |
| Intra-CV | 13.47% |

<u>Cmax</u>

| | |
|---|---|
| Ratio of Means % | 93.35 |
| Ratio of Geo Means % | 93.00 |
| Avg of Individual Ratios % | 95.73 |
| 90% C.I. | 86%-99% |
| Intra-CV | 16.07% |

<u>Tmax</u>

Open Capsule Sprinkled on Applesauce
Capsules Intact

| Mean |
|---|
| 13.7 hours |
| 13.5 hours |

Fig. 10A

Diltiazem AUCt Results

Formulation According to Embodiment of Invention

| Subject | Open Capsules Sprinkled on Applesauce (A) | | Capsule Intact (B) | | (A:B) Ratio |
|---|---|---|---|---|---|
| | AUCt | Log Cmax | AUCt | Log Cmax | |
| 1 | 3937.18 | 8.28 | 3251.62 | 8.09 | 1.21 |
| 2 | 3792.89 | 8.24 | 5502.18 | 8.61 | 0.69 |
| 3 | 1616.35 | 7.39 | 2358.22 | 7.77 | 0.69 |
| 4 | 8209.44 | 9.01 | 7954.29 | 8.98 | 1.03 |
| 5 | 2171.26 | 7.68 | 2452.78 | 7.80 | 0.89 |
| 6 | 5710.90 | 8.65 | 7082.30 | 8.87 | 0.81 |
| 7 | 1983.56 | 7.59 | 2624.03 | 7.87 | 0.76 |
| 8 | 3862.46 | 8.26 | 3114.53 | 8.04 | 1.24 |
| 9 | 6069.65 | 8.71 | 4585.60 | 8.43 | 1.32 |
| 10 | 3907.33 | 8.27 | 6393.14 | 8.76 | 0.61 |
| 11 | 3842.58 | 8.25 | 4292.30 | 8.36 | 0.90 |
| 12 | 4873.82 | 8.49 | 6493.87 | 8.78 | 0.75 |
| 13 | 2707.85 | 7.90 | 3922.90 | 8.27 | 0.69 |
| 14 | 2553.27 | 7.85 | 2159.88 | 7.68 | 1.18 |
| 15 | 2042.47 | 7.62 | 2902.70 | 7.97 | 0.70 |
| 16 | 4650.14 | 8.44 | 4769.32 | 8.47 | 0.98 |
| 17 | 3705.72 | 8.22 | 3464.89 | 8.15 | 1.07 |
| 19 | 7881.69 | 8.97 | 6851.45 | 8.83 | 1.15 |
| 21 | 6151.00 | 8.72 | 6292.65 | 8.75 | 0.98 |
| 22 | 2138.64 | 7.67 | 1933.52 | 7.57 | 1.11 |
| 23 | 3983.50 | 8.29 | 5177.74 | 8.55 | 0.77 |
| 24 | 3939.51 | 8.28 | 3517.56 | 8.17 | 1.12 |
| 25 | 2318.36 | 7.75 | 2016.26 | 7.61 | 1.15 |
| 27 | 2061.09 | 7.63 | 1928.02 | 7.56 | 1.07 |
| 28 | 2871.31 | 7.96 | 3312.87 | 8.11 | 0.87 |
| 29 | 4305.14 | 8.37 | 3559.57 | 8.18 | 1.21 |
| 30 | 3190.17 | 8.07 | 3565.88 | 8.18 | 0.89 |
| 31 | 3422.16 | 8.14 | 3012.17 | 8.01 | 1.14 |
| 33 | 4906.47 | 8.50 | 5206.52 | 8.56 | 0.94 |
| 34 | 2969.19 | 8.00 | 3255.28 | 8.09 | 0.91 |
| Mean | 3859.17 | 8.17 | 4098.47 | 8.24 | 0.96 |
| SD | 1664.90 | 0.42 | 1708.24 | 0.41 | 0.20 |
| CV | 43.14 | 5.10 | 41.68 | 5.03 | 20.69 |
| Median | 3817.74 | 8.25 | 3538.57 | 8.17 | 0.96 |
| Geo Mean | 3546.16 | 8.16 | 3773.43 | 8.23 | 0.94 |

Test/Ref Ratio
Ratio of Means %    94.16
Ratio of Geo Means %    93.98
Avg of Individual Ratios    0.96
90% C.I.    88%-99%
Intra-CV    13.47%

Fig. 10B

Diltiazem Cmax Results

Formulation According to Embodiment of Invention

| Subject | Open Capsule Sprinkled on Applesauce (A) | | | Capsule Intact (B) | | | (A:B) Ratio |
|---|---|---|---|---|---|---|---|
| | Tmax | Cmax | Log Cmax | Tmax | Cmax | Log Cmax | |
| 1 | 13.0 | 184.35 | 5.22 | 13.0 | 228.99 | 5.43 | 0.81 |
| 2 | 14.0 | 192.44 | 5.26 | 12.0 | 286.72 | 5.66 | 0.67 |
| 3 | 13.0 | 103.87 | 4.64 | 12.0 | 127.07 | 4.84 | 0.82 |
| 4 | 10.0 | 372.93 | 5.92 | 8.0 | 298.05 | 5.70 | 1.25 |
| 5 | 14.0 | 107.71 | 4.68 | 16.0 | 147.84 | 5.00 | 0.73 |
| 6 | 13.0 | 244.87 | 5.50 | 15.0 | 315.48 | 5.75 | 0.78 |
| 7 | 14.0 | 115.23 | 4.75 | 16.0 | 135.27 | 4.91 | 0.85 |
| 8 | 13.0 | 257.26 | 5.55 | 15.0 | 179.11 | 5.19 | 1.44 |
| 9 | 8.0 | 232.12 | 5.45 | 10.0 | 194.37 | 5.27 | 1.19 |
| 10 | 16.0 | 172.20 | 5.15 | 15.0 | 281.81 | 5.64 | 0.61 |
| 11 | 13.0 | 177.41 | 5.18 | 8.0 | 181.17 | 5.20 | 0.98 |
| 12 | 13.0 | 225.55 | 5.42 | 10.0 | 327.23 | 5.79 | 0.69 |
| 13 | 15.0 | 135.86 | 4.91 | 15.0 | 213.37 | 5.36 | 0.64 |
| 14 | 15.0 | 154.65 | 5.04 | 14.0 | 135.94 | 4.91 | 1.14 |
| 15 | 12.0 | 114.81 | 4.74 | 15.0 | 181.80 | 5.20 | 0.63 |
| 16 | 15.0 | 294.21 | 5.68 | 13.0 | 296.58 | 5.69 | 0.99 |
| 17 | 15.0 | 187.32 | 5.23 | 15.0 | 183.62 | 5.21 | 1.02 |
| 19 | 16.0 | 385.36 | 5.95 | 15.0 | 376.57 | 5.93 | 1.02 |
| 21 | 15.0 | 318.06 | 5.76 | 10.0 | 276.15 | 5.62 | 1.15 |
| 22 | 14.0 | 114.40 | 4.74 | 14.0 | 97.24 | 4.58 | 1.18 |
| 23 | 12.0 | 260.20 | 5.56 | 12.0 | 346.74 | 5.85 | 0.75 |
| 24 | 14.0 | 211.61 | 5.35 | 16.0 | 202.88 | 5.31 | 1.04 |
| 25 | 14.0 | 155.98 | 5.05 | 15.0 | 125.66 | 4.83 | 1.24 |
| 27 | 16.0 | 79.66 | 4.38 | 16.0 | 67.35 | 4.21 | 1.18 |
| 28 | 16.0 | 124.76 | 4.83 | 16.0 | 165.01 | 5.11 | 0.76 |
| 29 | 15.0 | 225.58 | 5.42 | 10.0 | 164.02 | 5.10 | 1.38 |
| 30 | 14.0 | 166.54 | 5.12 | 15.0 | 165.41 | 5.11 | 1.01 |
| 31 | 15.0 | 134.14 | 4.90 | 14.0 | 135.19 | 4.91 | 0.99 |
| 33 | 13.0 | 282.10 | 5.64 | 16.0 | 275.33 | 5.62 | 1.02 |
| 34 | 10.0 | 118.88 | 4.78 | 15.0 | 155.15 | 5.04 | 0.77 |
| Mean | 13.7 | 195.00 | 5.19 | 13.5 | 208.90 | 5.27 | 0.96 |
| SD | 1.9 | 80.09 | 0.41 | 2.5 | 80.27 | 0.41 | 0.23 |
| CV | 13.8 | 41.07 | 7.83 | 18.3 | 38.43 | 7.73 | 24.25 |
| Median | 14.0 | 180.88 | 5.20 | 15.0 | 182.71 | 5.21 | 0.99 |
| Geo Mean | 13.5 | 180.09 | 5.18 | 13.3 | 193.65 | 5.25 | 0.93 |

Test/Ref Ratio
Ratio of Means %            93.35
Ratio of Geo Means %     93.00
Avg of Individual Ratios      0.96
90% C.I.                        86%-99%
Intra-CV                    16.07%

CHRONOTHERAPEUTIC DILTIAZEM FORMULATIONS AND THE ADMINISTRATION THEREOF

This application is a continuation-in-part application of U.S. patent application Ser. No. 09/465,338 filed Dec. 17, 1999 now abandoned claiming priority from Canadian Patent Application No. 2,292,247 filed Dec. 10, 1999. This application also claims priority from a Canadian Patent Application filed May 4, 2000.

FIELD OF INVENTION

This invention relates to once daily preparations comprising Diltiazem and pharmaceutically acceptable salts thereof, such as the hydrochloride salt, suitable for evening administration to patients suffering hypertension and/or angina. This invention also relates to a method for evening administration of such once daily preparations to patients for the treatment of the patients' hypertension and/or angina.

BACKGROUND OF THE INVENTION

Diltiazem, a benzothiazepine, is an orally active calcium channel blocker (calcium-antagonist) with relatively high selectivity for vascular smooth muscle that is effective in the treatment of hypertension and angina pectoris. Today, persons having these conditions take prescribed once daily preparations of Diltiazem generally to maintain constant levels of the drug in the body over a 24-hour period. Until recently the timing of the taking of the medicine wasn't considered an important consideration by the medical community. Doctors generally did not take into account the natural circadian variation in the body's physiological functions. Researchers have now found that the timing of the taking of a medicine can affect the way the human body responds to the medicine. The science of treating the human body taking into account the natural circadian variation is Chronotherapeutics. Chronotherapeutics relies on the practice of delivering the correct amount of medication to the correct site of action at the most appropriate time period for the particular disease or condition. In man, blood pressure does not remain constant during day and night. Early in the morning blood pressure begins to rise from the low levels reached during sleep. Increases in blood pressure are accompanied by increases in heart rate caused by the chemicals generated by the body and delivered into the blood stream. Epidemiological studies have indicated that the greatest incidence of heart problems such as stroke, heart attack, myocardial ischemia and sudden cardiac death occur during the early morning waking hours when the blood pressure is rising in response to the natural circadian rhythm. After normally rising in the morning, blood pressure remains elevated during the day until generally early evening when it starts to fall to its lowest level during sleep.

In one study, evening medication with Diltiazem for treatment of hypertension for effect the next morning has been stated to be more efficacious than other dosage schedules. *Administration Time-Dependent Effects of Diltiazem on The 24-Hour Blood Pressure Profile of Essential Hypertension Patients*, Isao Kohno et al. (Chronobiology International 14(1), 71–84, (1997.) In the report of the study, Herbesser R™ (200 mg) was identified as the Diltiazem preparation. Herbesser R™ is a Diltiazem formulation comprising a mixture of immediate release diltiazem—containing microspheres and sustained release diltiazem—containing coated microspheres. According to the report, following a single dose (200 mg) administration, the time of peak plasma diltiazem concentration occurred at 12.5 hours after administration. The peak plasma diltiazem concentration Cmax in the persons studied was 107 mg/ml. Following multiple dosages of 200 mg Diltiazem given over 7 days, the time of peak plasma diltiazem concentration (Cmax) was at 10 hours after administration. Cmax was 154 mg/ml.

However a careful review of the report shows inconsistencies which cannot support the authors' conclusions. Particularly at page 80, the best results shown in the graph are with respect to morning treatment with this formulation. Moreover at page 82, the authors themselves acknowledge the study cannot lead to reliable conclusions "because the number of patients was too small". Further, an immediate release portion of the dosage in the order of 15% is not desirable for evening administration. When the blood pressure is naturally at its lowest, not only is there no need for further reduction at that time, but such reduction can harm the patient. Particularly, if the blood pressure is reduced below a minimum the patient is put at a greater risk for cardiovascular accidents including stroke. Further, the 15% immediate release diltiazem is no longer available when needed.

In *A comparative study of the steady-state pharmacokinetics of immediate-release and controlled-release diltiazem tablets*, O. R. Leeuwenkamp et al., Eur. J. Clin. Pharmacol (1994) 46:243–247, controlled release properties and relative systemic availabilities of two dosages of the same controlled release diltiazem tablet formulation were studied by comparing them as steady state with those of an immediate release formulation. In the testing, the diltiazem plasma concentration increased slowly from about 6 hours after the evening dose of both CR tablets (Diltiazem CR 90 mg and Diltiazem CR 120 mg) resulting in relatively high plasma concentrations in the early morning hours. The clinicians concluded that twice-daily treatment with diltiazem CR tablets can replace thrice-daily treatment with a conventional diltiazem IR tablet. According to the clinicians "The early morning rise of the diltiazem plasma concentration, which might lead to a lower incidence of ischemic events, may be an important clinical advantage of both CR tablets."

On Apr. 22, 1998, Searle Canada announced that its Chronovera (R) (controlled onset extended-release verapamil) a high blood pressure medication was now available in Canada. Chronovera (R) was, according to Searle Canada, specifically designed to work with the body's natural circadian variations and was designed to be taken once-a-day just before bedtime. Chronovera provided 24-hour blood pressure control but was designed to deliver peak concentrations of verapamil in the morning when the blood pressure, heart rate and incidence of cardiovascular events were highest. According to Searle Canada, simply changing the time you take the drug your physician has prescribed will not provide the same safety and effectiveness that is designed specially for chronotherapy using verapamil. According to Searle Canada, its Chronovera (R) is unlike traditional medications including extended-release (XL) and sustained-release (SR) formulations which are usually prescribed in doses that maintain relatively constant levels of the drug in the body over a 24-hour period or attempt to maintain relatively constant levels of the drug in the body over a 24-hour period. According to Searle Canada, the prior formulations do not take into account the natural circadian variations in the body's physiological functions.

Sustained-release, once-daily diltiazem formulations have been taught which may be considered the traditional medication (according to Searle Canada). They appear not to give the benefits meant to be achieved by chronotherapy.

For example, in *Pharmacokinetic Properties and Antihypertensive Efficacy of Once-Daily Diltiazem*, J. G. Kelly et al., Journal of Cardio-Vascular Pharmacology, 17:6:957–963, (1991), the controlled-release formulation of diltiazem released a proportion of the diltiazem relatively rapidly with the remainder released over a period extending to 24-hours. During in vitro dissolution testing 15% of the diltiazem in the dosage form was released in the first two hours, 54% was released in the first six hours, 89% in the first 13 hours and all of the remainder was released between 13 and 24 hours after administration. The diltiazem capsules contained either 120 mg or 240 mg of diltiazem. It should be noted that no difference is shown between the placebo and dosages in the article at wake-up (between 5:00 a.m. and 8:00 a.m.).

U.S. Pat. No. 4,960,596 discloses slow release 12 hour diltiazem formulations whose dissolution, when measured in accordance with United States Pharmacopoeia 21, purports to be within broad limits (between 5% and 35% after one hour, between 15% and 40% after two hours, between 20% and 50% after three hours, between 30% and 75% after four hours, between 40% and 80% after six hours and between 55% and 95% after eight hours). The examples in the patent, however, provide more specific range limitations specifying range limitations for the formulations exemplified such as at column 4, lines 8–10 and column 5, lines 60–62. In the first series of examples the release into aqueous medium was measured using the method of USP No. 21 of 10%–20% after one hour, 30%–35% after four hours and 60%–75% after eight hours. In the later examples, the release into aqueous medium was measured using the method of USP No. 21 at 15%–35% after one hour, 55%–75% after four hours, 75%–95% after eight hours. These formulations were, however, twice a day (b.i.d.) formulations.

A series of patents have issued to Elan Corporation p.l.c. involving controlled absorption diltiazem pellet formulations for oral administration in which each pellet has a core comprising diltiazem or a pharmaceutically acceptable salt thereof in association with a specified organic acid covered by an outer membrane which permits release of diltiazem from aqueous medium in accordance with U.S. Pharmacopoeia XX (Paddle Method) in buffered media at pH 1.5, pH 4.0 and pH 7.0. These are U.S. Pat. Nos. 4,721,619; 4,891, 230; 4,894,240; 4,917,899; 5,002,776; 5,219,621; 5,336, 504; 5,364,620 and 5,616,345.

In U.S. Pat. No. 4,721,619, dissolution rates of the pellets of examples are found at column 4, lines 41–49 and column 5, lines 5–12. The formulations, however are for 12 hour. The formulations of U.S. Pat. No. 4,891,230 are also for administration every 12 hours.

U.S. Pat. No. 4,894,240 purports to provide formulations for once-daily administration and specifies a general dissolution pattern at column 2, lines 43–52 and a more restricted dissolution pattern at column 3, lines 3–12. The dissolution rates are determined according to U.S. Pharmacopoeia XXI in 0.05M KCl at pH 7.0 and at 100 r.p.m. The examples of the patent, however, provide a more limited dissolution pattern under U.S. Pharmacopoeia XXI (Paddle Method) at column 7, lines 30–34 and 47–51, at column 8, lines 16–20, 32–36 and 49–53 and at column 8, line 66—column 9, line 5. Similar examples are provided at columns 9, 10, 11 and 12. Nothing is taught with respect to formulations suitable as chronotherapeutics.

U.S. Pat. Nos. 4,917,899, 5,364,620 and 5,616,345 are to the same effect. So are the remaining Elan patents. Nothing in these patents teach formulations suitable as chronotherapeutics.

U.S. Pat. No. 5,529,790 purports to teach a delayed sustained-release pharmaceutical preparation in which a water-soluble drug core is surrounded by a hydratable diffusion barrier which delays drug release for about two to ten hours. While diltiazem hydrochloride dissolution patterns were provided in accordance with the U.S.P. basket dissolution method specified, no Cmax or the timing of the maximum blood levels is provided. The dissolution rates of the active are not appropriate for a suitable chronotherapeutic (see also U.S. Pat. Nos. 5,376,384 and 5,478,573).

U.S. Pat. Nos. 5,288,505 and 5,529,791 relate to extended-release galenical formulations of diltiazem or pharmaceutically acceptable salts thereof which comprise beads in which the active ingredient is in association with a wetting agent and which beads are coated by a microporous membrane. The Cmax of some formulations given in the patents provide for a Cmax after about 8–12 hours. Where the dosing of the formulations of the patents yields maximum diltiazem blood plasma levels (Cmax) of about 145 ng/ml, the Cmax is at about or less than 8 hours.

The applicants are also aware of a formulation marketed under the trade mark Tiazac™ a diltiazem HCl 24-hour sustained-release formulation based on teachings of U.S. Pat. Nos. 5,529,791 and 5,288,505.

Following chronic administration of Tiazac (240 mg once daily), the average peak plasma Diltiazem concentration (Cmax) is 183 ng/ml (multiple dosage) which occurred after about 7 hours past dose administration. Tiazac™ provides a bioavailability of approximately 59% of the total Diltiazem in the first 12 hours and 41% in the second 12 hours (after 12 hours, 59%; after 16 hours 77% and after 20 hours 90%).

In an article entitled *Effect of Morning Versus Evening Dosing of Diltiazem on Myocardial Ischemia Detected by Ambulatory Electrocardiographic Monitoring in Chronic Stable Angio Pectoris*, PRA KASH, C. Deedwanian et al., The American Journal of Cardiology, Vol. 80, Aug. 15, 1997, p. 421–425, the authors compare a.m. and p.m. dosing without using an appropriate dosage form for p.m. The Tmax is achieved between 2–6 hours at steady state.

In an article *The Influence of Time Administration on the Pharmacokinetics of a Once A Day Diltiazem Formulation: Morning Against Bedtime*, Jean Thiffault et al., Biopharmaceutics & Drug Disposition, Vol. 17, 107–115 (1996), the once-a-day diltiazem formulation given at 2200 hours for seven days gave according to the article "significantly higher plasma concentrations of diltiazem in the early morning hours when the incidence of cardiovascular events is higher". The diltiazem dosages comprise 240 mg taken at 10:00 p.m. (22:00 hours) and maximum concentrations (Cmax) were achieved of 120 ng/ml after about six–eight hours of dosing. Unfortunately, the proposed system covers only the period from 2:00 a.m. to 8:00 a.m. To be a true chronotherapeutic, the time period covered should be between about 6:00 a.m. and noon. Moreover, this formulation when given at night leads to significantly lower bioavailability than if given in the morning.

It is therefore an object of this invention to provide diltiazem preparations suitable for once-a-day administration in the evening for providing effective dosage amounts in the blood of diltiazem in the morning when blood pressure begins to rise from the low levels reached during sleep, so as to be suitable as a chronotherapeutic preparation.

It is a further object of this invention to provide a method of administration of the diltiazem preparations suitable as a chronotherapeutic so as to be effective in the morning at a time when the patient has most need of the diltiazem preparation. Further and other objects of the invention will be realized by those skilled in the art from the following summary of the invention and detailed description of embodiments thereof.

SUMMARY OF THE INVENTION

According to one aspect of the invention, there is provided a controlled-release Galenical preparation (such as a tablet and a capsule) of pharmaceutically acceptable Diltiazem including the pharmaceutically acceptable salts thereof, such as the hydrochloride salt, suitable for evening dosing every 24 hours containing from about 120 mg to about 540 mg or more (as desired) of the form of Diltiazem associated with excipients to provide controlled (sustained) release of the form of Diltiazem for providing a Cmax of Diltiazem in the blood at between about 10 hours and about 15 hours (preferably about 11–about 13 hours) after administration, the preparation comprising the form of Diltiazem in oral sustained-release dosage form in which the Diltiazem is adapted to be released after administration over a prolonged period of time and the preparation is adapted to release the Diltiazem (i) into an aqueous medium at the following rates measured using the method of United States Pharmacopoeia No. XXIII (at 100 rpm in 900 ml of water):
  (a) between about 1% and about 15% after about 2 hours, preferably between about 4% and about 8% after 2 hours;
  (b) between about 7% and about 35% after about 4 hours preferably between about 16% and about 21% after 4 hours;
  (c) between about 30% and about 58% after about 8 hours preferably between about 44% and about 52% after 8 hours;
  (d) between about 55% and about 80% after about 14 hours preferably between about 69% and about 76% after about 14 hours; and
  (e) in excess of about 75% after about 24 hours and preferably more than about 85% after 30 hours.

and/or (ii) into a buffered medium (such as, for example, phosphate buffer (U.S.P.)) having a pH between about 5.5 and about 6.5, preferably about 5.8 at the following rates measured using the method of United States Pharmacopoeia No. XXIII at 100 rpm in 900 ml of the buffered medium:
  (a) between about 1% and about 25% after about 2 hours, preferably between about 4% and about 15% after 2 hours;
  (b) between about 7% and about 45% after about 4 hours preferably between about 16% and about 30% after 4 hours;
  (c) between about 30% and about 68% after about 8 hours preferably between about 44% and about 62% after 8 hours;
  (d) in excess of about 75% after about 24 hours and preferably more than 80% after 24 hours.

Preferably no initial retard or delay is built into the preparation retarding/delaying release of Diltiazem from the preparation. Preferably the release rate from the preparation of the Diltiazem is less than about 15% of the total active per hour during dissolution. The preparation may be a diffusion controlled preparation such as, for example, a preparation incorporating the use of microgranules found, for example, in capsules and tablets; tablets; and coated tablets.

The preparation may comprise a plurality of microgranules or pellets, each microgranule comprising a central core or bead containing the form of diltiazem coated with a microporous membrane. The microgranules or pellets may be included in a capsule which dissolves when swallowed to release the microgranules or pellets. The preparation may also comprise a tablet in which the microgranules have been compressed to form the tablet. When compressed into tablet form, wax placebo beads (as known by persons skilled in the art) are preferably included to absorb the shock placed on the microgranules (core and membrane) during the tableting process. By doing so, the integrity of the microgranules containing the Diltiazem active remains intact and the release rate from the preparation is not affected. The tablet may also be coated or uncoated. The preparation may also comprise a sustained-release tablet coating from which preparation the Diltiazem is released. In this regard, the sustained release coating may be applied (sprayed onto) to each tablet.

Where the preparation comprises microgranules or pellets (for example) in the capsule or tablet (made, for example, by compressing the microgranules (with preferably wax placebo beads)), the central core may comprise Diltiazem or a pharmaceutically acceptable salt thereof associated with a wetting agent. The Diltiazem may be mixed (in whole or in part) with the wetting agent or may not be mixed with the wetting agent. The wetting agent assists to maintain the solubility of the Diltiazem in each microgranule, ensuring that the solubility of the Diltiazem is unaffected by the pH of the gastrointestinal tract or other adverse conditions which each of the microgranules of the preparation will meet in the gastrointestinal tract.

If the Diltiazem and/or pharmaceutically acceptable salt is not mixed with the wetting agent then the microporous membrane should comprise with suitable adjuvants, a water-dispersible or water-soluble polymer (such as HPMC) and a water-, acid- and base-insoluble polymer of a neutral acrylic polymer such as Eudragit NE30D (a neutral copolymer of acrylic acid ethyl ester and acrylic acid methyl ester) which hydrates the microgranule (including core). If the composition comprises a mixture of the Diltiazem and/or pharmaceutically acceptable salt with the wetting agent, the microporous membrane is preferably the same. However, it may also comprise any suitable membrane which gives to the preparation the required dissolution characteristics.

In this regard, the preferred microporous membrane comprises Eudragit NE30D and hydroxypropylmethylcellulose. This membrane will hydrate the core within the microporous membrane which, for example, may contain diltiazem surrounding a neutral pellet of sugar. The Eudragit NE30D in the membrane expands when it encounters gastrointestinal fluid to greater than 365% of its original size (elongation). This expandability of the membrane gives it the ability to hydrate the membrane and core. The mechanism of release is postulated to be that the membrane will swell while the fluids penetrate and hydrate the core and dissolve the diltiazem and wetting agent. This mechanism is, it is thought, driven by the concentration gradient through the membrane (high concentration inside and low concentration outside).

When Eudragit RS and Eudragit RL are combined to form the microporous membrane, the membrane can expand only very little before breakage or fracturing. The reason is that Eudragit RS expands minimally (about 6%) before the membrane material breaks or fractures changing its release mechanism from the core. Thus, the mechanism of release from this membrane is thought to be by "washing" the diltiazem through pores created when a plasticizer incorporated in the membrane is released in the gastrointestinal fluid. The diltiazem at the outer surface of the core would be washed from the core through the pores of the microporous membrane, then the diltiazem next presenting itself to the fluids after "washing" of the uppermost (outermost) diltiazem, and so on.

Instead of the wetting agent, any other suitable dissolution agent may be used to assist the release of the Diltiazem from the preparation. For example, instead of the preferred surface active (wetting) agent (surfactant), an organic acid (such as adipic acid, ascorbic acid, citric acid, fumaric acid, malic acid, succinic acid, tartaric acid and the like) may be incorporated in the core. In this regard, the presence of the organic acid in the core permits the diltiazem in the core to dissolve when the composition passes into the higher pH regions of the gastrointestinal tract of the intestine at which pH diltiazem is much less soluble. One of the membranes which may be used (though not preferred) is the combination of Eudragit RS and Eudragit RL disclosed in U.S. Pat. No. 4,721,619. (See column 1, lines 55–68 and column 2, lines 44–68.) The '619 patent also mentions the use of hydroxypropylmethylcellulose as a water-soluble membrane. The mechanism of release in this case is not by hydration of the core but rather by "washing" the Diltiazem through the pores created in the membrane (for example when the plasticizer in the membrane is released in the gastrointestinal fluid).

The Diltiazem may be present in the core in, for example, the hydrochloride salt form, in which event no dissolution agent may be required in the core.

Suitable preparations such as capsules of the microgranules making up the total Diltiazem active present, may comprise, in the core, Diltiazem hydrochloride between about 50% and about 85% (% w/w of the total preparation (for example, about 69% to about 73%)), a wetting agent (such as sucrose stearate) between about 2% and about 25% (% w/w of the total preparation) (for example about 7% to about 8%) together with suitable adjuvants in the core, and in the membrane between about 0.1% and about 2% of the total preparation of water-soluble and/or water-dispersible polymer such as hydroxypropylmethylcellulose (for example about 0.3% to about 0.6%), and between about 5% and about 20% (% w/w of the preparation) of a neutral copolymer of acrylic acid ethyl ester and acrylic acid methyl ester (such as Eudragit NE30D) (for example about 7% to about 11%).

The microgranules may also be compressed into tablets using suitable excipients. The percentages may be as described above. The tablets may be manufactured, as discussed above, using the microgranules with wax placebo beads and compressing the combination into tablets in the presence of, for example, hydrogenated vegetable oil, sodium starch glycolate and silicone dioxide which have been blended with the microgranules and wax placebo beads before tableting. The tablets may then be coated or uncoated.

According to another aspect of the invention, there is provided a controlled-release Galenical preparation (such as a tablet and a capsule) of pharmaceutically acceptable Diltiazem including the pharmaceutically acceptable salts thereof, such as the hydrochloride salt, suitable for evening dosing every 24 hours containing from about 120 mg to about 540 mg or more (as desired) of the form of Diltiazem associated with excipients to provide controlled (sustained) release of the form of Diltiazem for providing a Cmax of Diltiazem in the blood at between about 10 hours and about 15 hours (preferably about 11–about 13 hours) after administration, the preparation comprising the form of Diltiazem in oral sustained-release dosage form in which the Diltiazem is adapted to be released after administration over a prolonged period of time and exhibits when given to humans (i) a higher bioavailability when given at night compared to when given in the morning without food according to FDA guidelines or criteria and (ii) bioequivalence when given in the morning with food (such as a standardized FDA breakfast) and without food according to the same FDA guidelines or criteria.

The FDA guidelines are those entitled:

"GUIDANCE ORAL EXTENDED (CONTROLLED) RELEASE DOSAGE FORMS IN VIVO BIOEQUIVALENCE AND IN VITRO DISSOLUTION TESTING" prepared under 21 CFR 10.90(b)(9) by Shrikant V. Dighe, Ph.D., Director, Division of Bioequivalence Office of Generic Drugs dated Sep. 3, 1993 and concurred by Roger L. Williams, M.D., Director, Office of Generic Drugs, Center for Drug Development Research dated Sep. 4, 1993 which is incorporated herein by reference; and "GUIDANCE STATISTICAL PROCEDURES FOR BIOEQUIVALENCE STUDIES USING A STANDARD TWO-TREATMENT CROSSOVER DESIGN" prepared under 21 CFR 10.90(b)(9) by Mei-Ling Chem, Ph.D., Division of Bioequivalence Review Branch II dated Jun. 12, 1992 and Rabindra Patnaik, Ph.D., Division of Bioequivalence Review Branch II dated Jun. 26, 1992, approved by Shrikant V. Dighe, Ph.D., Director, Division of Bioequivalence dated Jun. 29, 1992 and concurred by Roger L. Williams, M.D., Director, Office of Generic Drugs dated Jun. 29, 1992 which is incorporated herein by reference.

In small part the said "GUIDANCE" documents provide as follows:

Pharmacokinetic Analysis of Data: Calculation of area under the plasma concentration-time curve to the last quantifiable concentration ($AUC_{0-t}$) and to infinity ($AUC_{0-\infty}$), $C_{max}$, and $T_{max}$ should be performed according to standard techniques.

Statistical Analysis of Pharmacokinetic Data: The log transformed AUC and $C_{max}$ data should be analyzed statistically using analysis of variance. These two parameters for the test product should be shown to be within 80–125% of the reference product using the 90% confidence interval. See also Division of Bioequivalence Guidance Statistical Procedures for Bioequivalence Studies Using a Standard Two-Treatment Crossover Design.

Statistical Analysis of Pharmacokinetic Data: The log transformed AUC and $C_{max}$ data should be analyzed statistically using analysis of variance. These two parameters for the test product should be shown to be within 80–125% of the reference product using the 90% confidence interval. Fluctuation for the test product should be evaluated for comparability with that for the reference product. For further information on statistical analysis, see the Division of Bioequivalence Guidance Statistical procedures for Bioequivalence Studies Using a Standard Two-Treatment Crossover Design.

2. Multiple Dose Studies

At a minimum, the following pharmacokinetic parameters for the substance(s) of interest should be measured in a multiple dose bioequivalence study:

a. Area under the plasma/blood concentration—time curve from time zero to time τ over a dosing interval at steady state ($AUC_{0-\tau}$), where τ is the dosing interval.
b. Peak drug concentration ($C_{max}$) and the time to peak drug concentration ($T_{max}$), obtained directly from the data without interpolation, after the last dose is administered.
c. Drug concentrations at the end of each dosing interval during steady state ($C_{min}$).
d. Average drug concentration at steady state ($C_{av}$), where $C_{av}=AUC_{0-\tau}/\tau$.
e. Degree of fluctuation (CF) at steady state, where $DF=100\% \times (C_{max}-C_{min})/C_{av}$.

Evidence of attainment of steady state for the test and reference products should be submitted in the bioequivalence study report.

B. Statistical Analysis

Parametric (normal-theory) general linear model procedures are recommended for the analysis of pharmacokinetic data derived from in vivo bioequivalence studies. An analysis of variance (ANOVA) should be performed on the pharmacokinetic parameters AUC and $C_{max}$ using General Linear Models (GLM) procedures of SAS (4) or an equivalent program. Appropriate statistical models pertaining to the design of the bioequivalence study should be employed. For example, for a conventional two-treatment, two-period, two-sequence (2×2) randomized crossover study design, the statistical model often includes factors accounting for the following sources of variation:

1. Sequence (sometimes called Group or Order)
2. Subjects, nested in sequences
3. Period (or Phase)
4. Treatment (sometimes called Drug or Formulation)

The sequence effect should be tested using the [subject (sequence)]mean square from the ANOVA as an error term. All other main effects should be tested against the residual error (error mean square) from the ANOVA. The LSMEANS statement should be used to calculate least squares means for treatments. The ESTIMATE statement in SAS should be used to obtain estimates for the adjusted differences between treatment means and the standard error associated with these differences.

The two one-sided hypotheses at the α=0.05 level of significance should be tested for AUC and $C_{max}$ by constructing the 90% confidence interval for the ratio between the test and reference averages.

III. Logarithmic Transformation of Pharmacokinetic Data

A. Statistical Assumptions

The assumptions underlying the ANOVA are (5):
1. Randomization of samples
2. Homogeneity of variances
3. Additivity (linearity) of the statistical model
4. Independency and normality of residuals In bioequivalence studies, these assumptions can be interpreted as follows:
1. The subjects chosen for the study should be randomly assigned to the sequences of the study.
2. The variances associated with the two treatments, as well as between the sequence groups, should be equal or at least comparable.
3. The main effects of the statistical model, such as subject, sequence, period and treatment effect for a standard 2×2 crossover study, should be additive. There should be no interactions between these effects.
4. The residuals of the model should be independently and normally distributed. In other words, data from bioequivalence studies should have a normal distribution.

If these assumptions are not met, additional steps should be taken prior to the ANOVA including data transformation to improve the fit of the assumptions or use of a nonparametric statistical test in place of ANOVA. However, the normality and constant variance assumptions in the ANOVA model are known to be relatively robust, i.e., small or moderate departure from each (or both) of these assumptions will not have a significant effect on the final result.

B. Rationale for Log Transformation

1. Clinical Rationale

In a meeting in September 1991, the Generic Drugs Advisory Committee (GDAC) concluded that the primary comparison of interest in a bioequivalence study was the ratio rather than the difference between average parameter data from the test and reference formulations. Using log transformation, the general linear statistical model employed in the analysis of bioequivalence data allows inferences about the difference between the two means on the log scale, which can then be retransformed into inferences about the ratio of the two averages (means or medians) on the original scale. Log transformation thus achieves the general comparison based on the ratio rather than the difference (6).

2. Pharmacokinetic Rationale

Westlake (7,8) observed that a multiplicative model is postulated for pharmacokinetic parameters in bioavailability/bioequivalence studies, i.e., AUC and $C_{max}$ (but not $T_{max}$). Assuming that elimination of the drug is first order and only occurs from the central compartment, the following equation holds after an extravascular route of administration:

$$AUC_{0-\infty} = FD/CL$$
$$= FD/(VK_e)$$

where F is the fraction absorbed, D is the administered dose, and FD is the amount of drug absorbed. CL is the clearance of a given subject which is the product of the apparent volume of distribution (V) and the elimination rate constant ($K_e$).[2]

[2]Note that a more general equation can be written for any multi-compartmental model as $AUC_{0-\infty}=FD/(V_{d\beta}\lambda_z)$ where $V_{d\beta}$ is the volume of distribution relating drug concentration in plasma or blood to the amount of drug in the body during the terminal exponential phase, and $\lambda_z$ is the terminal slope of the concentration-time curve.

The use of AUC as a measure of the amount of drug absorbed thus involves a multiplicative term (CL) which might be regarded as a function of the subject. For this reason, Westlake contends that the subject effect is not additive if the data is analyzed on the original scale of measurement.

Logarithmic transformation of the AUC data will bring the CL ($VK_e$) term into the equation in an additive fashion.

$$lnAUC_{0-\infty}=lnF+lnD-lnV-lnK_3$$

Similar arguments were given for $C_{max}$. The following equation applies for a drug exhibiting one compartmental characteristics:

$$C_{max}=(FD/V)\times e^{-K_e\Delta T_{max}}$$

where again F, D and V are introduced into the model in a multiplicative manner. However, after logarithmic transformation, the equation becomes $$lnC_{max}=lnF+1ND-1NV-K_eT_{max}$$

Log transformation of the $C_{max}$ data also results in the additive treatment of the V term.

3. Statistical Rationale

Logarithmic transformation of the data from bioequivalence studies can be used to circumvent the use of estimates of the reference product average for computation of the confidence interval for the ratio of product averages. This is an advantage for the cases where a least squares estimate for the reference product mean is not well defined. Standard parametric methods are ill-suited to making inferences about the ratio of two averages, though some valid methods do exist (9). Log transformation changes the problem to one of making inferences about the difference (on the log scale) of two averages, for which the standard methods are well suited.

Many biological data correspond more closely to a log-normal distribution than to a normal distribution. The plasma concentration data including the derived parameters AUC and $C_{max}$ tend to be skewed, and their variances tend to increase with the means. Log transformation is likely to remedy this situation and make the variances independent of the mean. In addition, frequency distributions skewed to the left (with a long tail to the right) are often made more symmetrical by log transformation.

This argument is actually less persuasive than the argument based on the additivity of the statistical model because it is based largely on the between-subject distribution of AUC and $C_{max}$ values. For crossover studies, it is largely the within-subject distribution of values that determines the validity and efficiency of the standard parametric methods of analysis.

Despite the arguments regarding the effect of log transformation on normality of bioequivalence data, the division of Bioequivalence recognizes that the limited sample size (20–30 subjects) in a bioequivalence study precludes a reliable determination of the underlying normal distribution of the data set either with or without log transformation.

C. General Procedures

Based on the arguments in the preceding section, the Division of Bioequivalence recommends that the pharmacokinetic parameters AUC and $C_{max}$ be log transformed. Firms are not encouraged to test for normality of data distribution after log transformation, nor should they employ normality of data distribution as a justification for carrying out the statistical analysis on the original scale.

Robustness of a balanced study to nonnormality of the data plus use of log transformation will be adequate in most cases.

If a firm believes that the data of a particular bioequivalence study should be statistically analyzed on the original scale rather than the log scale, justification based upon a sound scientific rationale, as well as the statistical methods to be used, ought to be submitted to and reviewed by the Division of Bioequivalence.

Thus according to another aspect of the invention, the results of biostudies employing a formulation according to an embodiment of the invention, clearly show that when given at different times (P.M. or A.M. dosing) and under different conditions (with and without food) though they achieve their maximum bioavailability at the same $T_{max}$, when the formulation is given at night (no food) a higher bioavailability (for example a significantly higher bioavailability exceeding 25% ($C_{max}$) is attained than when given in the morning without food (according to FDA guidelines) and bioequivalence when given with food or without food in the morning according to the FDA guidelines.

According to another aspect of the invention, a method of treatment of a patient's hypertension and/or angina is provided comprising administration of a preparation of Diltiazem described above, to the patient in the evening for example at about 7:00–about 11:00 p.m. for effective treatment of the patient's hypertension and/or angina the next morning, for example between about 6:00 a.m. and about noon.

According to another embodiment of the invention a method of treatment of a patient's hypertension and/or angina is provided comprising administration of a preparation which exhibits a higher bioavailability (exceeding, for example, 25%) when given at night compared to when given in the morning without food according to FDA guidelines or criteria and bioequivalence when given with food (for example given a standardized FDA breakfast) and without food according to the same FDA guidelines or criteria.

Thus a 24-hour diltiazem preparation is provided wherein the Cmax of diltiazem in the blood is provided from about 10–15 hours after administration of a single dosage to a patient or about 9–15 hours after multiple dosages over a number of days and displays the dissolution pattern described above determined according to USP 23, page 1791 using Apparatus 1. Apparatus 1 is described as consisting of the following:

a covered vessel made of glass or other inert, transparent material[1]; a motor; a metallic drive shaft; and a cylindrical basket. The vessel is partially immersed in a suitable water bath of any convenient size that permits holding the temperature inside the vessel at 37 ±0.5° during the test and keeping the bath fluid in constant, smooth motion. No part of the assembly, including the environment in which the assembly is placed, contributes significant motion, agitation, or vibration beyond that due to the smoothly rotating stirring element. Apparatus that permits observation of the specimen and stirring element during the test is preferable. The vessel is cylindrical, with a hemispherical bottom. It is 160 to 175 mm high, its inside diameter is 98 to 106 mm, and its nominal capacity is 1000 mL. Its sides are flanged at the top. A fitted cover may be used to retard evaporation.[2] The shaft is positioned so that its axis is not more than 2 mm at any point from the vertical axis of the vessel and rotates smoothly and without significant wobble. A speed-regulating device is used that allows the shaft rotation speed to be selected and maintained at the rate specified in the individual monograph, within +4%.

Shaft and basket components of the stirring element are fabricated of stainless steel, type 316 or equivalent, to the specifications shown in FIG. 1. Unless otherwise specified in the individual monograph, use 40-mesh cloth. A basket having a gold coating 0.0001 inch (2.5 µm) thick may be used. The dosage unit is placed in a dry basket at the beginning of each test. The distance between the inside bottom of the vessel and the basket is maintained at 25±2 mm during the test.

[1] The materials should not sorb, react, or interfere with the specimen being tested.
[2] If a cover is used, it provides sufficient openings to allow ready insertion of the thermometer and withdrawal of specimens.

(taken from USP 23)

According to another aspect of the invention, where the preparations comprise cores wherein the diltiazem is in association with a wetting agent, the wetting agent may be selected from:

sugars;

saccharose, mannitol, sorbitol;

lecithins;

$C_{12}$ to $C_{20}$ fatty acid esters of saccarose, commercialized under the name of sucroesters (Gattefosse, France) or under the name of crodesters (Croda, U.K.) such as sucrose stearate marketed under the trade name of Crodesta;

xylose esters or xylites;

polyoxyethylenic glycerrides;

esters of fatty acids and polyoxyethylene (Brijs, Renex and Eumulgines, Henkel, RFA);

sorbitan fatty acid esters (Span, Atlas, U.S.A.);

polyglycides-glycerides and polyglycides-alcohols esters (Gelucires, Gattefosse, France)

Metal salts such as NaCl or sodium lauryl sulphate

The microporous membrane may be of any suitable material or combination of materials known in the art. Where the wetting agent is in association with the diltiazem in the core and not mixed therewith, the microporous membrane should comprise a water-soluble or water dispersible polymer or copolymer such as hydroxypropylmethylcellulose and a water-, acid- and base-insoluble polymer such as a neutral copolymer of acrylic acid ethyl ester and acrylic acid methyl ester such as Eudragit NE30D. This enables the bead to be hydrated by the introduction of intestinal fluids into the bead hydrating the bead and therefore mixing the diltiazem and the wetting agent. The membrane itself, because of the fluids passing through the membrane, will swell. This membrane acts differently from membranes which do not swell. These other non-hydratable or swellable membranes may be made-up, for example, of water-soluble or water-dispersible polymers or copolymers and a water-, acid- and base-insoluble polymer such as Eudragit RS which swell less easily (owing to the reduced content in quaternary ammonium groups) and are only slightly permeable to active ingredients. This membrane is best suited for coating cores of Diltiazem mixed with a wetting agent or organic acid.

Among materials which may be used to make the microporous membranes, may be mentioned particularly polyacrylates and polymethacrylates of the Eudragit type, ethyl celluloses such as Ethocels from Dow U.S.A. and Aquacoat of FMC U.S.A., hydroxypropylmethylcellulose, hydroxyethylcellulose and hydroxypropylcellulose.

Additionally, adjuvants may be put in the formulation as required such as plastifying agents (plasticizer), pigments, fillers, lubricants and anti-foaming agents. For example talc and/or magnesium stearate may be used as a lubricant, dibutyl sebecate as plasticizer, titanium dioxide as a pigment, Tween 80 as an emulsifier and silicone oil as an anti-foaming agent.

The amount of the microporous membrane is adjusted to provide the sustained release characteristics described.

Thus embodiments of the invention have higher bioavailability (greater AUC and $C_{max}$ at the same time (T)) when given at night than given in the morning without food according to the FDA guidelines discussed previously and are bioequivalent when given in the morning with food to formulation given in the morning without food according to the FDA guidance.

BRIEF DESCRIPTION OF THE DRAWINGS

The invention will now be illustrated with reference to the following examples and with reference to the following Figures.

Preparations were manufactured according to the percentages and constituents set out below:

| Component | | % W/W |
|---|---|---|
| (1) | Diltiazem hydrochloride | 69–73 |
| (2) | Microcrystalline cellulose (Avicel ph101) | 8–9.5 |
| (3) | Povidone K30 | 1–2 |
| (4) | Sucrose stearate (crodesta F150) | 7–8 |
| (5) | Magnesium stearate NF | 0.5–2.5 |
| (6) | Talc USP | 0.5–5.0 |
| (7) | Titanium dioxide (USP) | 0.15–0.3 |
| (8) | Hydroxypropylmethylcellulose 2910 | 0.3–0.6 |
| (9) | Polysorbate 80 (tween) | 0.01–0.025 |
| (10) | Simeticone C emulsion USP (dry of 30%) | 0.01–0.015 |
| (11) | Eudragit NE30 D (dry of 30%) | 7–11 |
| (12) | Purified water USP | 0 |

Two Examples of preparations given the above percentages were made as 120 mg and 180 mg strengths of Diltiazem (as the HCl salt) in capsule form.

Example 2

| | Strength 120 mg capsule |
|---|---|
| (1) | 120.00 |
| (2) | 13.63–16.18 |
| (3) | 1.7–3.41 |
| (4) | 11.92–13.63 |
| (5) | 0.852–4.26 |
| (6) | 0.852–8.52 |
| (7) | 0.256–0.511 |
| (8) | 0.511–1.02 |
| (9) | 0.0170–0.0426 |
| (10) | 0.017–0.0256 |
| (11) | 11.92–18.74 |
| (12) | 0 |

Example 3

| | Strength 180 mg capsule |
|---|---|
| (1) | 180.00 |
| (2) | 20.44–24.27 |
| (3) | 2.56–5.11 |
| (4) | 17.88–20.44 |
| (5) | 1.278–6.388 |
| (6) | 1.278–12.78 |
| (7) | 0.383–0.767 |
| (8) | 0.7665–1.533 |
| (9) | 0.0256–0.0639 |
| (10) | 0.0255–0.383 |
| (11) | 17.886–28.106 |
| (12) | 0 |

Figure 3:
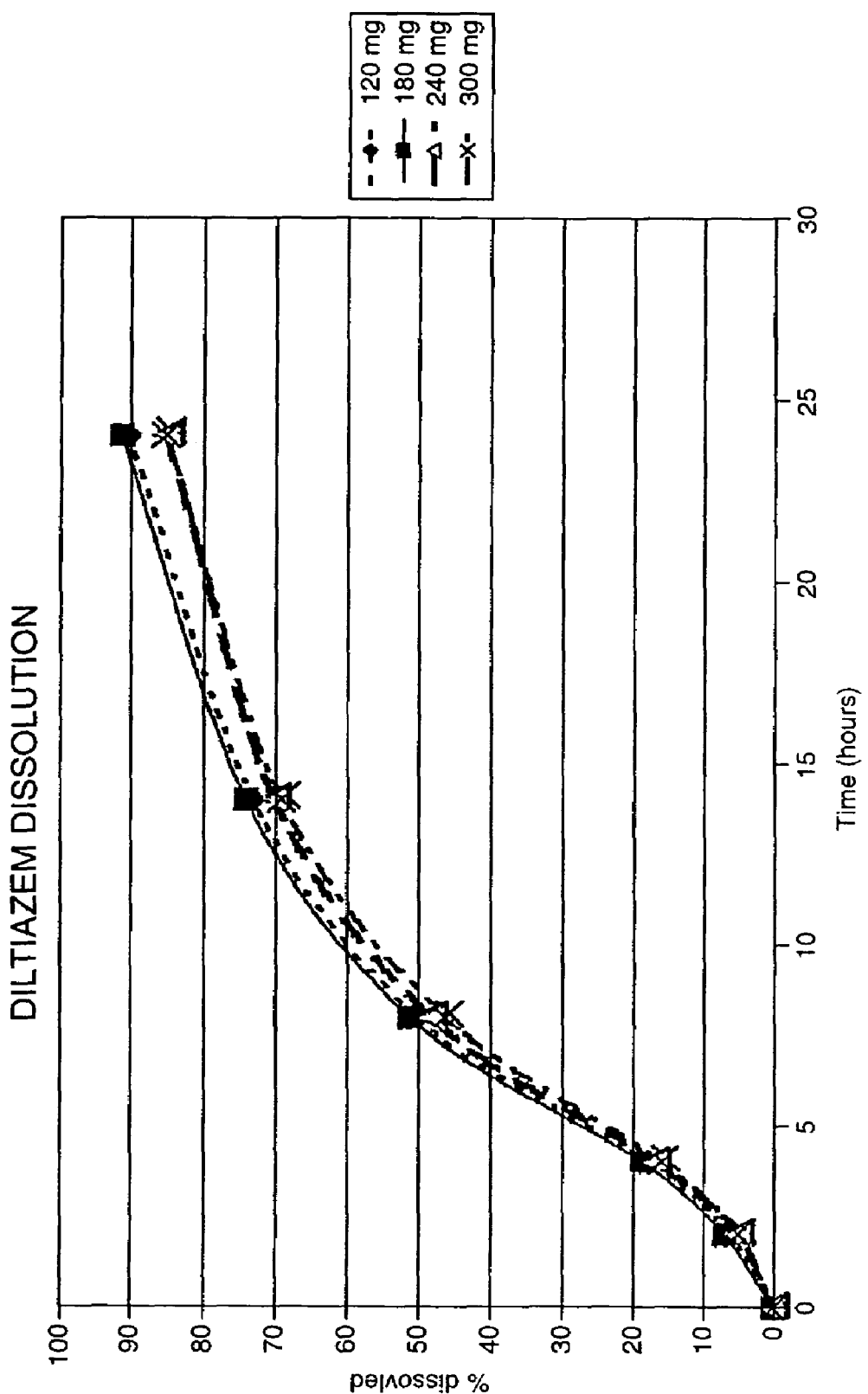
FIG. 3: is a graph illustrating dissolution profiles generated according to USP 23 using Apparatus 1 (baskets) at 100 r.p.m. in 900 ml of water for capsule preparations made according to embodiments of the invention (120 mg, 180 mg, 240 mg and 300 mg of Diltiazem active).
Figure 4:
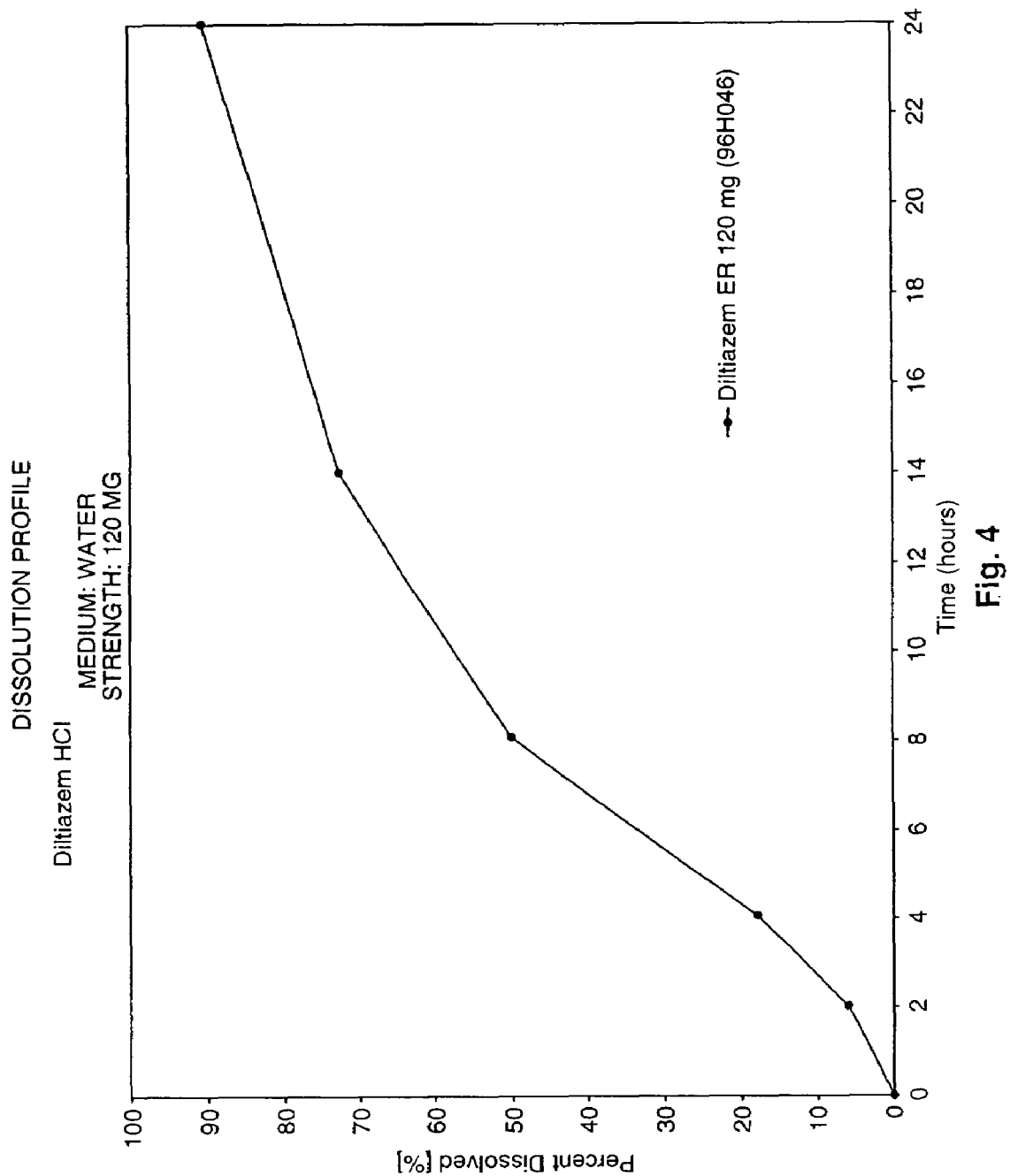
FIG. 4: illustrates the dissolution profile of a 120 mg capsule preparation of Diltiazem HCl in water according to USP 23 (Apparatus 1-baskets) according to an embodiment of the invention.
Figure 5:
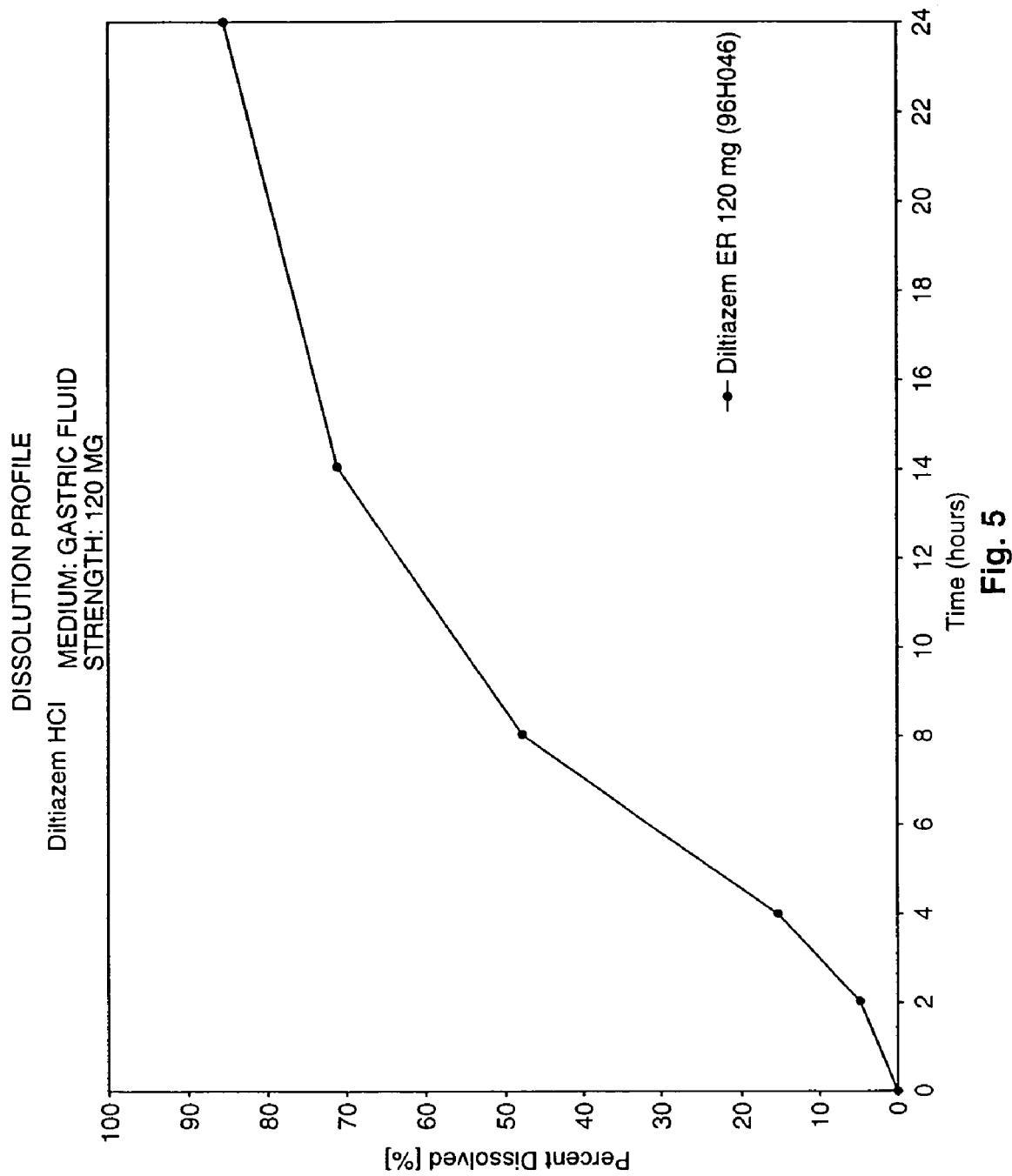
FIG. 5: illustrates the dissolution profile of a 120 mg capsule preparation of Diltiazem HCl in gastric fluid according to USP 23 (Apparatus 1-baskets) according to an embodiment of the invention.
Figure 6:
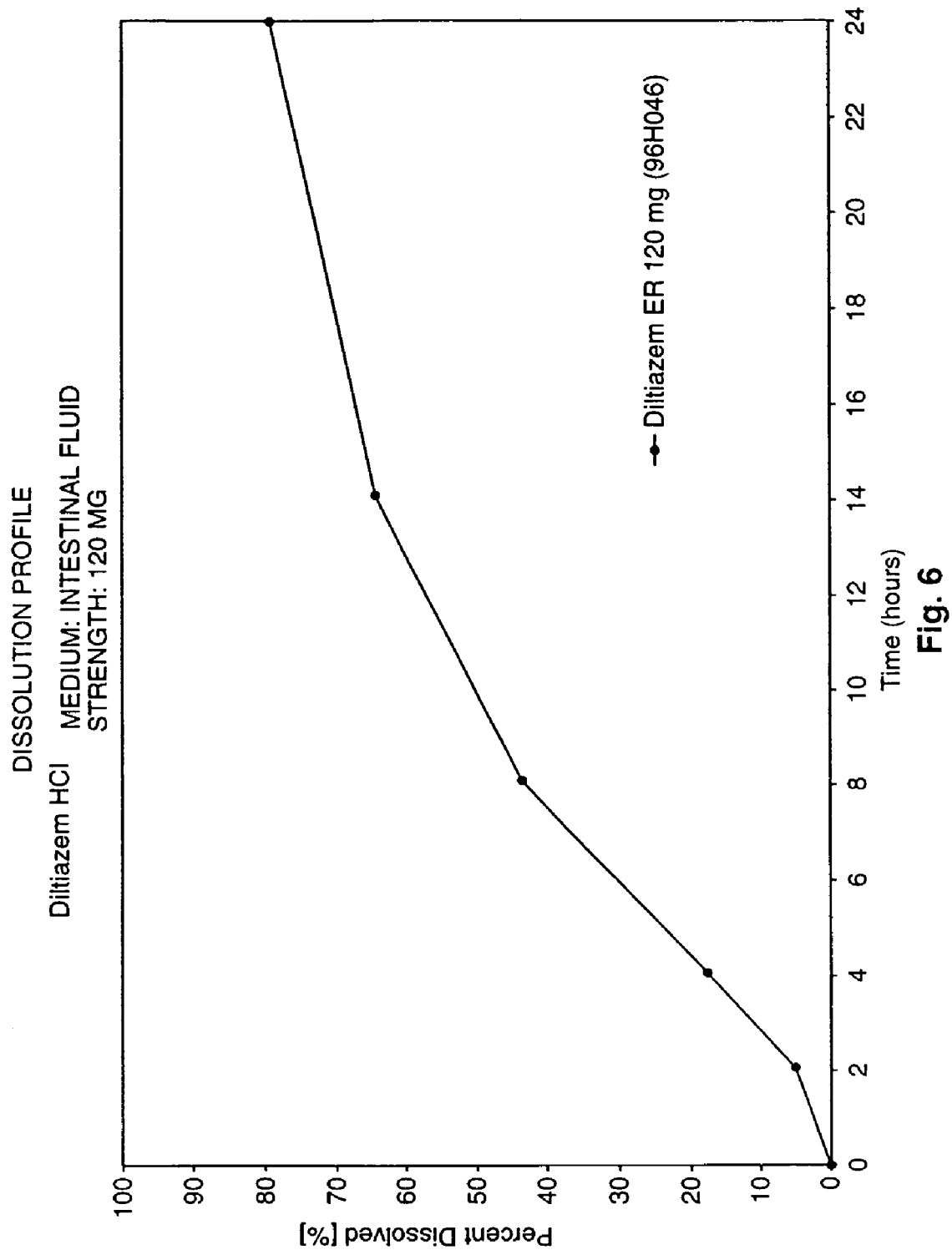
FIG. 6: illustrates the dissolution profile of a 120 mg capsule preparation of Diltiazem HCl in intestinal fluid according to USP 23 (Apparatus 1-baskets) according to an embodiment of the invention.

240 mg, 300 mg, 360 mg and 420 mg strength preparations in capsule form of Diltiazem (as the HCl salt) were also prepared having the same percentages. They provide the release patterns shown in FIG. 3. The dissolution profiles of all of the strengths were generated from biobatches of capsules using Apparatus 1 (baskets) at 100 RPM in 900 ml of water in accordance with USP 23.

Less than 20% of the formulation is dissolved after about four hours (for example between about 16%–21%) with less than about 10% dissolved in the first two hours (for example between about 4%–about 8%). Less than about 50% is released after 8 hours (for example between about 44%–52%). Less than about 73% is released after 14 hours (for example 69%–76%). Preferably in excess of about 85% is released after 24 hours.

Specifically, samples of 120 mg capsules of Diltiazem HCl (made according to the embodiment of the invention) had the following dissolution profile:

| | Percent Dissolved - Time Elapsed | | | | | | | | |
|---|---|---|---|---|---|---|---|---|---|
| | 2 h (%) | | 4 h (%) | | 8 h (%) | | 14 h (%) | | 24 h (%) | |
| | 5 | 8 | 19 | 19 | 49 | 49 | 72 | 72 | 88 | 88 |
| | 4 | 5 | 16 | 14 | 32 | 44 | 76 | 69 | 93 | 86 |
| | 5 | 6 | 18 | 16 | 50 | 49 | 72 | 73 | 88 | 90 |
| | 7 | 6 | 21 | 17 | 54 | 48 | 76 | 72 | 92 | 87 |
| | 5 | 8 | 17 | 19 | 51 | 50 | 74 | 74 | 92 | 91 |
| | 6 | 7 | 18 | 19 | 52 | 52 | 74 | 75 | 90 | 92 |
| Mean (%) | 6 | | 18 | | 50 | | 73 | | 90 | |
| RSD | 21.3 | | 10.5 | | 5.1 | | 2.7 | | 2.6 | |

Samples of 180 mg capsules of Diltiazem HCl (made according to an embodiment of the invention) had the following dissolution profiles:

| | Percent Dissolved - Time Elapsed | | | | | | | | |
|---|---|---|---|---|---|---|---|---|---|
| Lapsed Time | 2 h (%) | | 4 h (%) | | 8 h (%) | | 14 h (%) | | 24 h (%) | |
| | 8 | 7 | 21 | 20 | 52 | 52 | 76 | 73 | 91 | 89 |
| | 6 | 7 | 19 | 20 | 52 | 51 | 76 | 73 | 93 | 90 |
| | 5 | 6 | 16 | 18 | 48 | 50 | 72 | 72 | 89 | 90 |
| | 6 | 7 | 19 | 18 | 52 | 49 | 76 | 72 | 98 | 88 |
| | 7 | 7 | 20 | 19 | 51 | 51 | 73 | 74 | 91 | 91 |
| | 8 | 7 | 20 | 21 | 51 | 51 | 74 | 73 | 92 | 91 |
| Mean (%) | 7 | | 19 | | 51 | | 74 | | 91 | |
| RSD | 12.8 | | 7.4 | | 2.5 | | 2.1 | | 1.7 | |

Samples of 240 mg capsules of Diltiazem HCl (made according to an embodiment of the invention) had the following dissolution profiles:

| | Percent Dissolved - Time Elapsed | | | | | | | | |
|---|---|---|---|---|---|---|---|---|---|
| | 2 h (%) | | 4 h (%) | | 8 h (%) | | 14 h (%) | | 24 h (%) | |
| | 6 | 4 | 19 | 16 | 46 | 48 | 73 | 71 | 86 | 86 |
| | 6 | 5 | 18 | 15 | 48 | 45 | 70 | 68 | 85 | 84 |
| | 5 | 5 | 18 | 17 | 49 | 49 | 71 | 72 | 86 | 88 |
| | 4 | 7 | 16 | 18 | 46 | 48 | 68 | 71 | 83 | 87 |
| | 6 | 4 | 18 | 15 | 49 | 50 | 70 | 68 | 84 | 84 |
| | 6 | 6 | 18 | 17 | 48 | 48 | 70 | 71 | 85 | 86 |
| Mean (%) | 5 | | 17 | | 48 | | 70 | | 85 | |
| RSD | 18.5 | | 7.7 | | 2.9 | | 2.3 | | 1.7 | |

Samples of Diltiazem HCl capsules 300 mg (made according to an embodiment of the invention) had the following dissolution profile:

| Percent Dissolved - Time Elapsed | | | | | | | | | |
|---|---|---|---|---|---|---|---|---|---|
| 2 h (%) | | 4 h (%) | | 8 h (%) | | 14 h (%) | | 24 h (%) | |
| 3 | 4 | 16 | 16 | 46 | 45 | 68 | 67 | 83 | 83 |
| 6 | 5 | 17 | 16 | 49 | 45 | 73 | 67 | 90 | 83 |
| 6 | 5 | 16 | 16 | 46 | 46 | 69 | 68 | 84 | 84 |

-continued

| | Percent Dissolved - Time Elapsed | | | | |
|---|---|---|---|---|---|
| | 2 h (%) | 4 h (%) | 8 h (%) | 14 h (%) | 24 h (%) |
| | 5   5 | 16   16 | 46   46 | 69   69 | 83   87 |
| | 6   4 | 17   15 | 46   45 | 68   68 | 82   86 |
| | 5   5 | 17   17 | 46   47 | 69   70 | 84   87 |
| Mean (%) | 5 | 16 | 46 | 69 | 85 |
| RSD | 13.2 | 3.8 | 2.4 | 2.3 | 2.8 |

Additionally, the following Dissolution Profiles were obtained for the samples of 120 mg Diltiazem HCl Capsules:

Medium: Water

| | Diltiazem HCl Capsules | | |
|---|---|---|---|
| Hour | % Dissolved (Average of 12 capsules) | Range [%] | RSD |
| 2 | 6 | 4–8 | 17.6 |
| 4 | 18 | 14–21 | 9.8 |
| 8 | 50 | 44–54 | 5.1 |
| 14 | 73 | 69–76 | 2.8 |
| 24 | 90 | 86–93 | 2.5 |

Medium: Gastric Fluid

| | Diltiazem HCl Capsules | | |
|---|---|---|---|
| Hour | % Dissolved (Average of 12 capsules) | Range [%] | RSD |
| 2 | 5 | 3–6 | 18.8 |
| 4 | 16 | 14–18 | 9.0 |
| 8 | 49 | 47–52 | 3.5 |
| 14 | 73 | 71–75 | 1.8 |
| 24 | 87 | 85–89 | 1.5 |

Medium: Intestinal Fluid

| | Diltiazem HCl Capsules | | |
|---|---|---|---|
| Hour | % Dissolved (Average of 12 capsules) | Range [%] | RSD |
| 2 | 5 | 3–7 | 26.0 |
| 4 | 17 | 14–20 | 12.0 |
| 8 | 43 | 40–47 | 6.1 |
| 14 | 64 | 53–69 | 8.1 |
| 24 | 78 | 65–85 | 8.1 |

Other Dissolution Profiles were determined of embodiments of the invention

Medium—USP Water

Apparatus: USP #1 (baskets) at 100 rpm

| | Diltiazem 120 mg Capsules | | | | |
|---|---|---|---|---|---|
| TIME [h] | 2 | 4 | 8 | 14 | 24 |
| vessel 1 | 5% | 19 | 49 | 72 | 88 |
| vessel 2 | 4 | 16 | 52 | 76 | 93 |
| vessel 3 | 5 | 18 | 50 | 72 | 88 |
| vessel 4 | 7 | 21 | 54 | 76 | 92 |
| vessel 5 | 5 | 17 | 51 | 74 | 92 |
| vessel 6 | 6 | 18 | 52 | 74 | 90 |
| vessel 7 | 8 | 19 | 49 | 72 | 88 |
| vessel 8 | | 14 | 44 | 69 | 86 |
| vessel 9 | | 16 | 49 | 73 | 90 |
| vessel 10 | 6 | 17 | 48 | 72 | 87 |
| vessel 11 | 8 | 19 | 50 | 74 | 91 |
| vessel 12 | 7 | 19 | 52 | 75 | 92 |
| MEAN | 6% | 18 | 50 | 73 | 90 |
| SD | 1.3 | 1.9 | 2.6 | 2.0 | 2.3 |
| RSD | 21.3 | 10.5 | 5.1 | 2.7 | 2.6 |
| RANGE | 4–8 | 14–21 | 44–54 | 69–76 | 86–93 |

Medium—Gastric

Apparatus: USP #1 (baskets) at 100 rpm

| | Diltiazem 120 mg Capsules | | | | |
|---|---|---|---|---|---|
| TIME [h] | 2 | 4 | 8 | 14 | 24 |
| vessel 1 | 3 | 14 | 51 | 74 | 88 |
| vessel 2 | 6 | 17 | 48 | 72 | 85 |
| vessel 3 | 5 | 17 | 49 | 72 | 85 |
| vessel 4 | 5 | 15 | 48 | 72 | 87 |
| vessel 5 | 4 | | 47 | 71 | 86 |
| vessel 6 | 6 | 18 | 50 | 72 | 86 |
| vessel 7 | | 15 | 49 | 73 | 88 |
| vessel 8 | 4 | 14 | 48 | 71 | 86 |
| vessel 9 | 5 | 17 | 51 | 74 | 88 |
| vessel 10 | 6 | 18 | 52 | 74 | 88 |
| vessel 11 | 6 | 18 | | 75 | 89 |
| vessel 12 | 5 | 17 | 50 | 73 | 87 |
| MEAN | 5 | 16 | 49 | 73 | 87 |
| SD | 0.9 | 1.5 | 1.7 | 1.3 | 1.3 |
| RSD | 19.0 | 9.0 | 3.5 | 1.8 | 1.5 |
| RANGE | 3–6 | 14–18 | 47–52 | 71–75 | 85–89 |

Medium—Intestinal

Apparatus: USP #1 (baskets) at 100 rpm

| | Diltiazem 120 mg Capsules | | | | |
|---|---|---|---|---|---|
| TIME [h] | 2 | 4 | 8 | 14 | 24 |
| vessel 1 | 7 | 19 | 45 | 67 | 81 |
| vessel 2 | 4 | 14 | 40 | 64 | 79 |
| vessel 3 | 7 | 20 | 47 | 69 | 83 |
| vessel 4 | 5 | 19 | 46 | 68 | 83 |
| vessel 5 | | 17 | 41 | 58 | 69 |
| vessel 6 | | 17 | 45 | 69 | 83 |
| vessel 7 | 4 | 17 | 40 | 53 | 65 |

-continued

| | Diltiazem 120 mg Capsules | | | | |
|---|---|---|---|---|---|
| TIME [h] | 2 | 4 | 8 | 14 | 24 |
| vessel 8 | 5 | 17 | 42 | 65 | 78 |
| vessel 9 | 5 | | | 58 | 73 |
| vessel 10 | 5 | 17 | 47 | 68 | 85 |
| vessel 11 | 4 | 15 | 44 | 64 | 81 |
| vessel 12 | 4 | 15 | 43 | 64 | 81 |
| MEAN | 5 | 17 | 43 | 64 | 78 |
| SD | 1.2 | 2.0 | 2.7 | 5.2 | 6.4 |
| RSD | 25.9 | 13.0 | 6.1 | 8.1 | 8.1 |
| RANGE | 3–7 | 14–20 | 40–47 | 53–69 | 65–85 |

Briefly, the dosages in Examples 1 (120 mg) and 2 (180 mg), the 240 mg, 300 mg, 360 mg and 420 mg dosages were manufactured by mixing the core (bead) ingredients (diltiazem, microcrystalline cellulose, povidone, sucrose stearate) by introducing the components into a planetary mixer and granulating same and mixing with purified water. The plastic mass was then extruded to provide an extrudate. The extrudate was subsequently spheronized to produce diltiazem spheres in admixture with the wetting agent. The spheres (cores) were dried in an oven and sieved to the appropriate size cores or beads.

The membrane was prepared by mixing the hydroxypropylmethylcellulose, titanium dioxide, talc, magnesium stearate, Polysorbate 80 and Simethacone C emulsion and thereafter combined with the Eudragit NE30D and water. The spheronized cores were coated with the appropriate thickness of membrane by spraying the cores, coating same. Thus the cores (beads) were coated with the coating suspension to produce the microgranules or pellets. The microgranules or pellets were then dried.

In more detail the process combines Diltiazem Hydrochloride USP, Microcrystalline cellulose NF (Avicel PH 101), Povidone K30 USP and Sucrose Stearate (Crodesta F160) as follows:

The following were screened through a 1.9 mm screen and added to a mixer bowl:

Diltiazem
Avicel PH 101
Povidone K30.

To remove large agglomerates, the Crodesta 7.98 kg was screened through a 1.0–1.2 mm screen and added to the same mixing bowl. The items were then blended in an AMF blender at 50 RPM. 1 kg of the above dry blend was set aside to be used as dusting powder (Diltiazem Dusting Powder). The remainder of the blend was continued to be blended at 50 rpm until adequately granulated. The granulated material was then loaded into the hopper of an extruder (such as EXDCS100 or EXDS 60). The granulation was extruded and without breaking up the extrudate, the extrudate was collected. The extrudate was then spheronized into the cores (beads) of the desired size and were dusted as desired by the Diltiazem Dusting Powder set aside. The beads were then dried by spreading them on trays and drying in an oven set at about 57° C. The Drying Temp. was in the order of 55–60° C. for about 12 hours (in the order of 12–16 hours). The dried cores (beads) were sieved to collect those of appropriate size (0.7–1.4 mm).

A Eudragit NE30D and hydroxypropylmethylcellulose coating suspension, was made. The following:

Magnesium Stearate NF
Talc USP
Titanium Dioxide USP
Hydroxypropylmethylcellulose 2910 USP (Pharmacoat 606)
Polysorbate 80 NF (Tween 80)
Simethicone C Emulsion USP and pure water were combined within a Silverson Mixer. Water was first mixed with Polysorbate 80 and the Simethicone. The HPMC was then added, then titanium dioxide, then talc and then the Magnesium Stearate. The mixture was stored for 2 hours. The Eudragit NE30D was screened through a 0.310 mm sieve and added to the mixture.

The beads were then coated with the suspension by using an Aerocoater™ and spraying the beads (which have been preheated to 26° C.) with the coating suspension to achieve the desired thickness (about 0.05 mm). The beads were then dried by spreading on trays and drying at 40–45° C. for 10–12 hours.

Diltiazem HCl 300 mg capsules made according to an embodiment of the invention were tested in a single dose study to determine their bioavailability, their Cmax and Tmax, their rate and extent of absorption. Blood sampling for drug content analysis was carried out at 0.0 (predrug) 1, 2, 3, 4, 5, 6, 8, 10, 12, 14, 16, 18, 24, 30, 36, 42 and 48 hours post-drug. Vital sign and 12—Lead ECG monitoring were conducted at 0 (predrug) 2, 6, 8 and 12 hours post-drug. The following was determined from the plasma study:

| Mean Pharmacokinetic Parameters for Plasma Diltiazem (n = 41) | |
|---|---|
| Parameter | 1 × 300 mg Mean (% CV) |
| AUC (0-t)(ng.hr/mL) | 2703.83 (36.26) |
| AUG (0-inf.)(ng.hr/mL) | 2786.95 (36.39) |
| $C_{max}$ (ng/mL) | 146.33 (38.43) |
| $T_{max}$ (hours) | 13.17 (14.79) |
| $t_{1/2}$ (hours) | 6.96 (17.56) |
| $K_{el}$ (hour$^{-1}$) | 0.102 (15.983) |

| Mean Plasma Diltiazem Concentrations (ng/mL) (n = 41) | |
|---|---|
| SAMPLE TIME (HOURS) | 1 × 300 mg |
| 0.00 | 0.00 ± 0.00 |
| 1.00 | 0.76 ± 2.20 |
| 2.00 | 4.92 ± 3.87 |
| 3.00 | 10.97 ± 5.92 |
| 4.00 | 20.01 ± 10.77 |
| 5.00 | 33.46 ± 18.39 |
| 6.00 | 70.21 ± 37.03 |
| 8.00 | 95.43 ± 41.50 |
| 10.00 | 110.16 ± 47.43 |
| 12.00 | 132.84 ± 52.04 |
| 14.00 | 139.54 ± 55.11 |
| 16.00 | 126.35 ± 50.23 |
| 18.00 | 105.74 ± 40.86 |
| 24.00 | 62.84 ± 24.20 |
| 30.00 | 43.92 ± 16.94 |
| 36.00 | 25.67 ± 11.46 |
| 42.00 | 13.40 ± 7.37 |
| 48.00 | 7.50 ± 4.46 |

| Mean Pharmacokinetic Parameters for Plasma Diltiazem (n = 36) | |
|---|---|
| Parameter | Geometric Mean Arithmetic Mean (C.V.) 1 × 300 mg |
| AUC (0-t hours)(ng.hr/mL) | 2682.87 |
|  | 2872.06 (38.44) |
| AUC (0-x)(ng.hr/mL) | 1955.92 |
|  | 2075.00 (35.63) |
| AUC (0-infinity)(ng.hr/mL) | 2847.57 |
|  | 3055.19 (39.05) |
| $C_{max}$ (ng/mL) | 134.96 |
|  | 144.00 (37.17) |
| $T_{max}$ (hours)** | 13.00 (2.92) |
| $t_{1/2}$ (hours)* | 8.69 (22.85) |
| $K_{el}$ (hour$^{-1}$)* | 0.084 (22.860) |

*These are arithmetic means (CV %).
**This is median (±S.D.).

Figure 1:
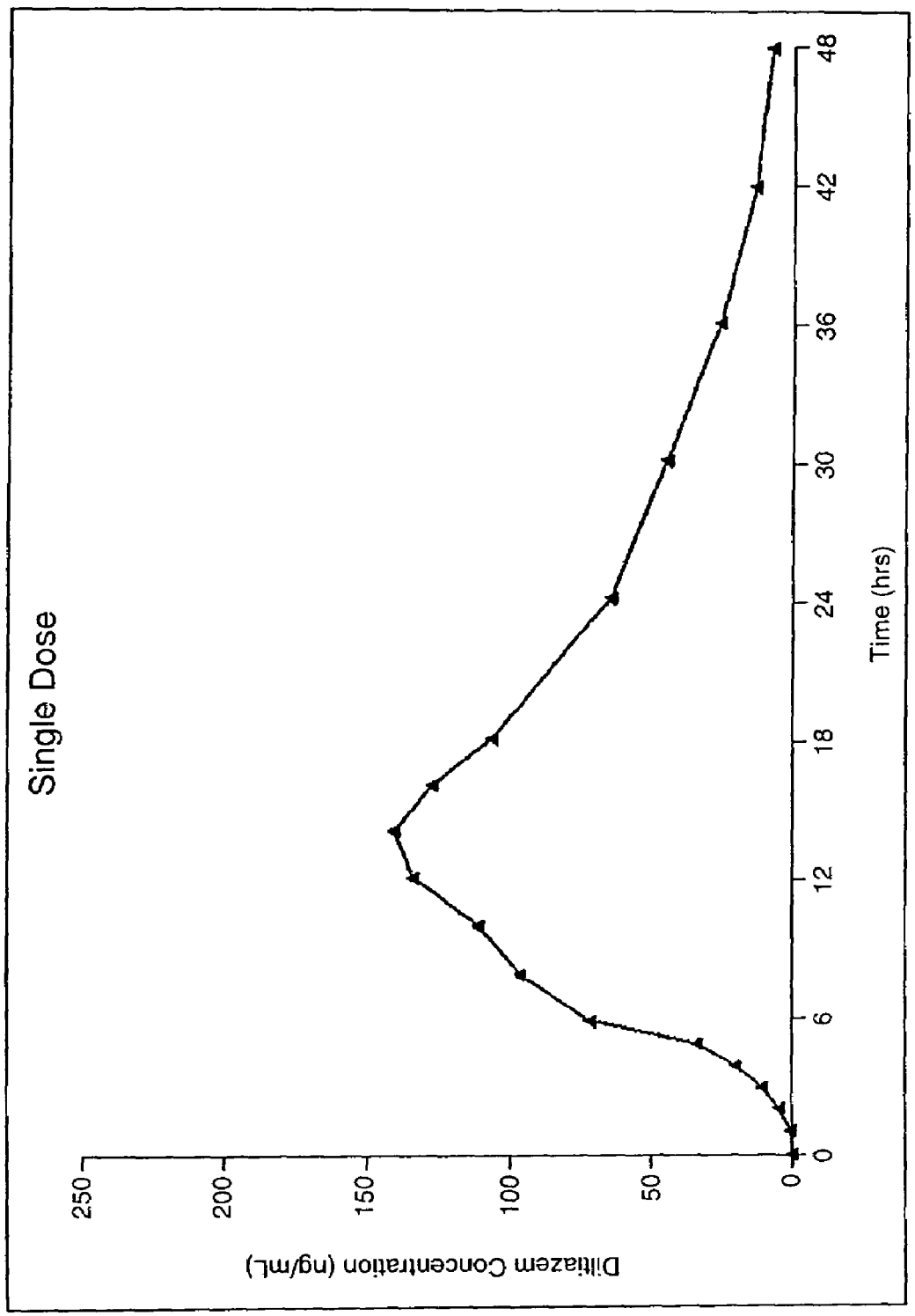
FIG. 1: is a graph illustrating the Diltiazem Concentration (ng/mL) in the blood after a specified period after a single dose of a 300 mg Diltiazem capsule preparation made according to an embodiment of the invention.
Figure 2:
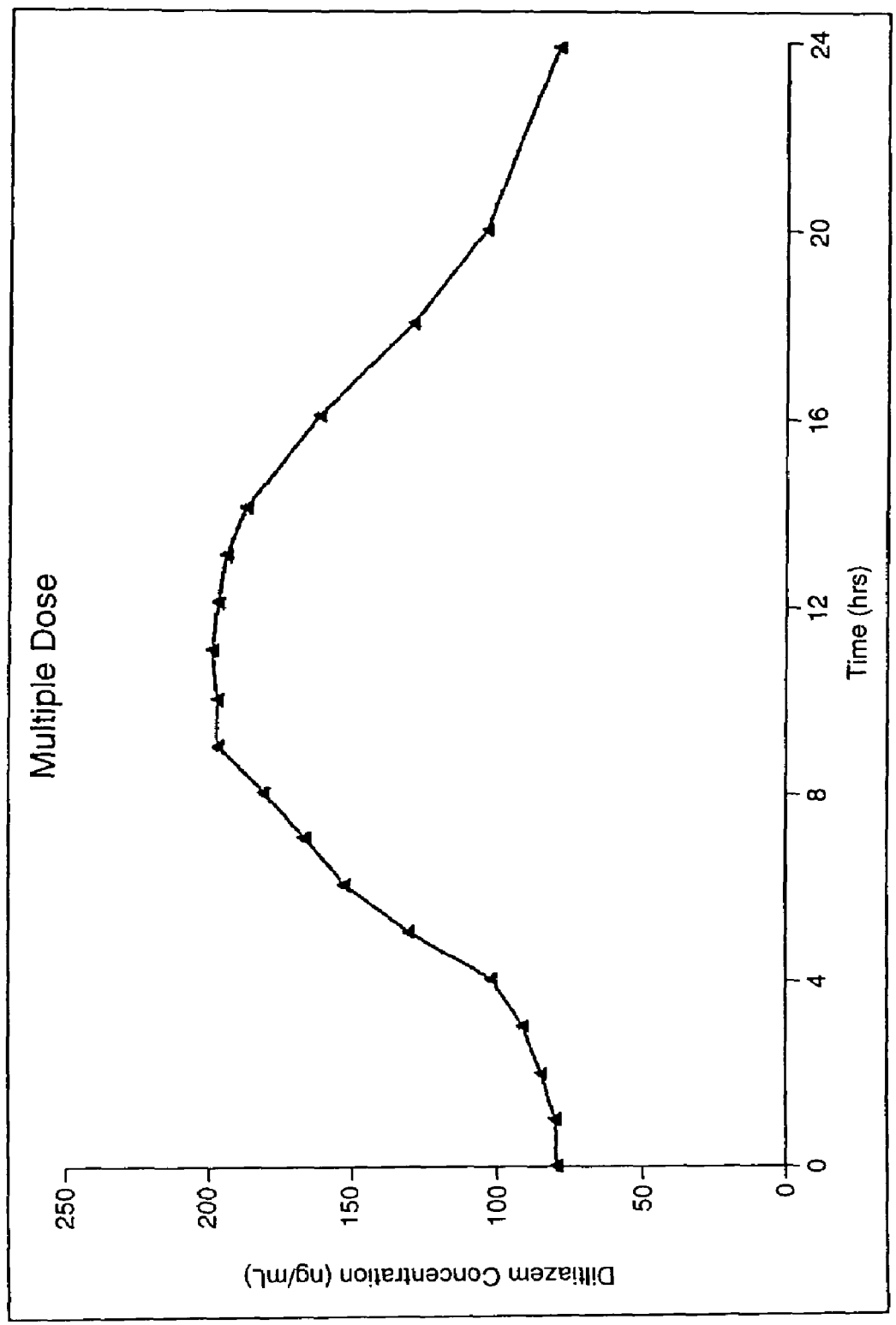
FIG. 2: is a graph illustrating the Diltiazem Concentration (ng/mL) in the blood over a 24-hour period after giving multiple doses of the same 300 mg Diltiazem capsules referred to with respect to FIG. 1 but over a number of days.
Figure 7:
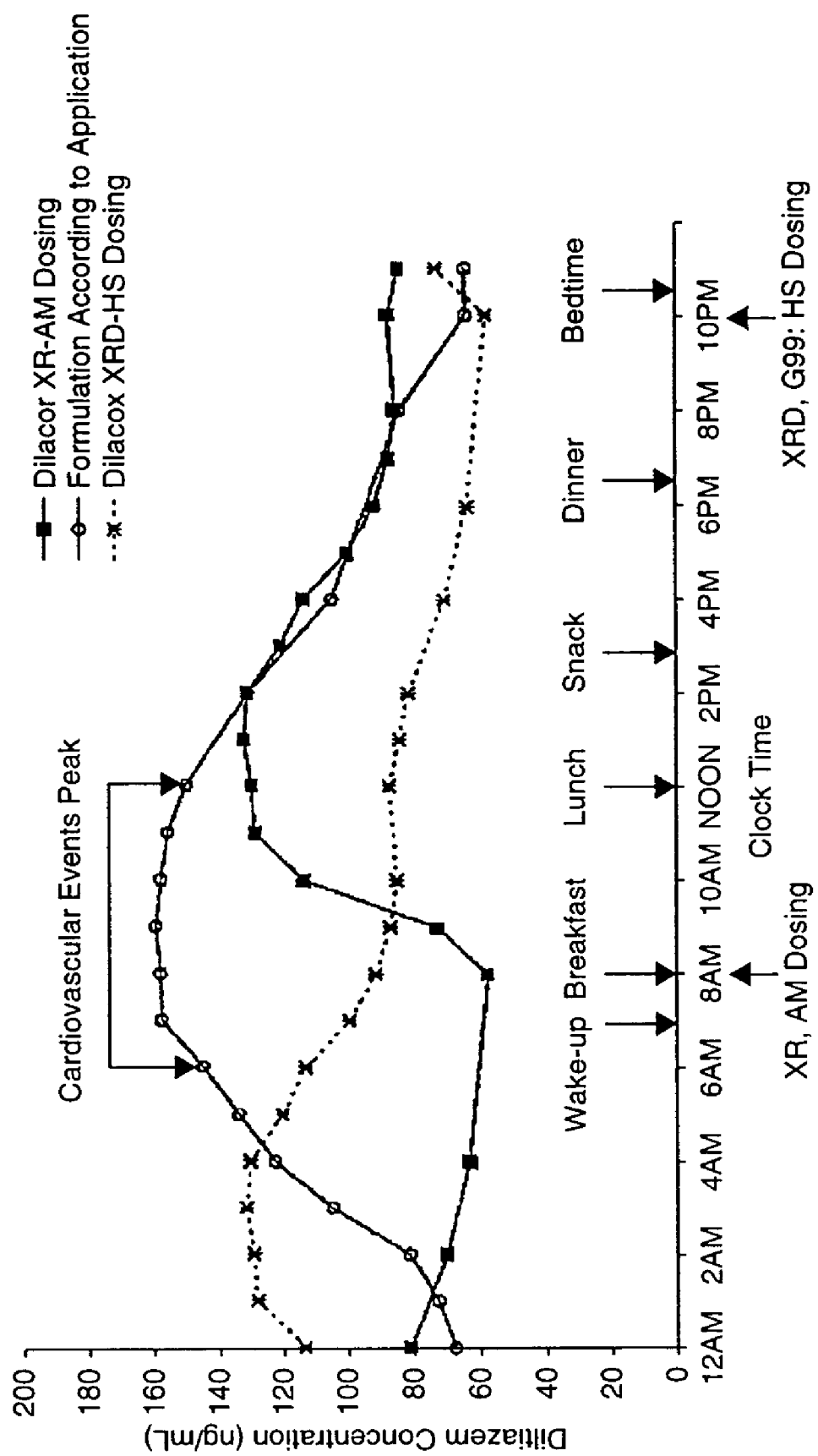
FIG. 7: is a graphic comparison of the blood level concentrations of a preparation (240 mg) made according to an embodiment of the invention and Dilacor (240 mg), a 24-hour oral sustained release dosage form of Diltiazem.

With reference to FIGS. 1 and 2, it is clear the 300 mg capsule preparation made according to an embodiment of the invention provides the appropriate Diltiazem blood levels at the appropriate time to be suitable for administration as a chronotherapeutic—being given in the evening to provide effective concentrations of Diltiazem the following morning. This suitability is illustrated with reference to FIGS. 7 and 8. In FIG. 7, the 240 mg Diltiazem preparation made according to the embodiment of the invention provides elevated blood levels that are effective all morning for effective treatment of the patient with Diltiazem. However, the Dilacor formulation (given either in the evening or the following morning) does not protect the patient from 6:00 a.m.–noon, the more dangerous period.

Figure 8:
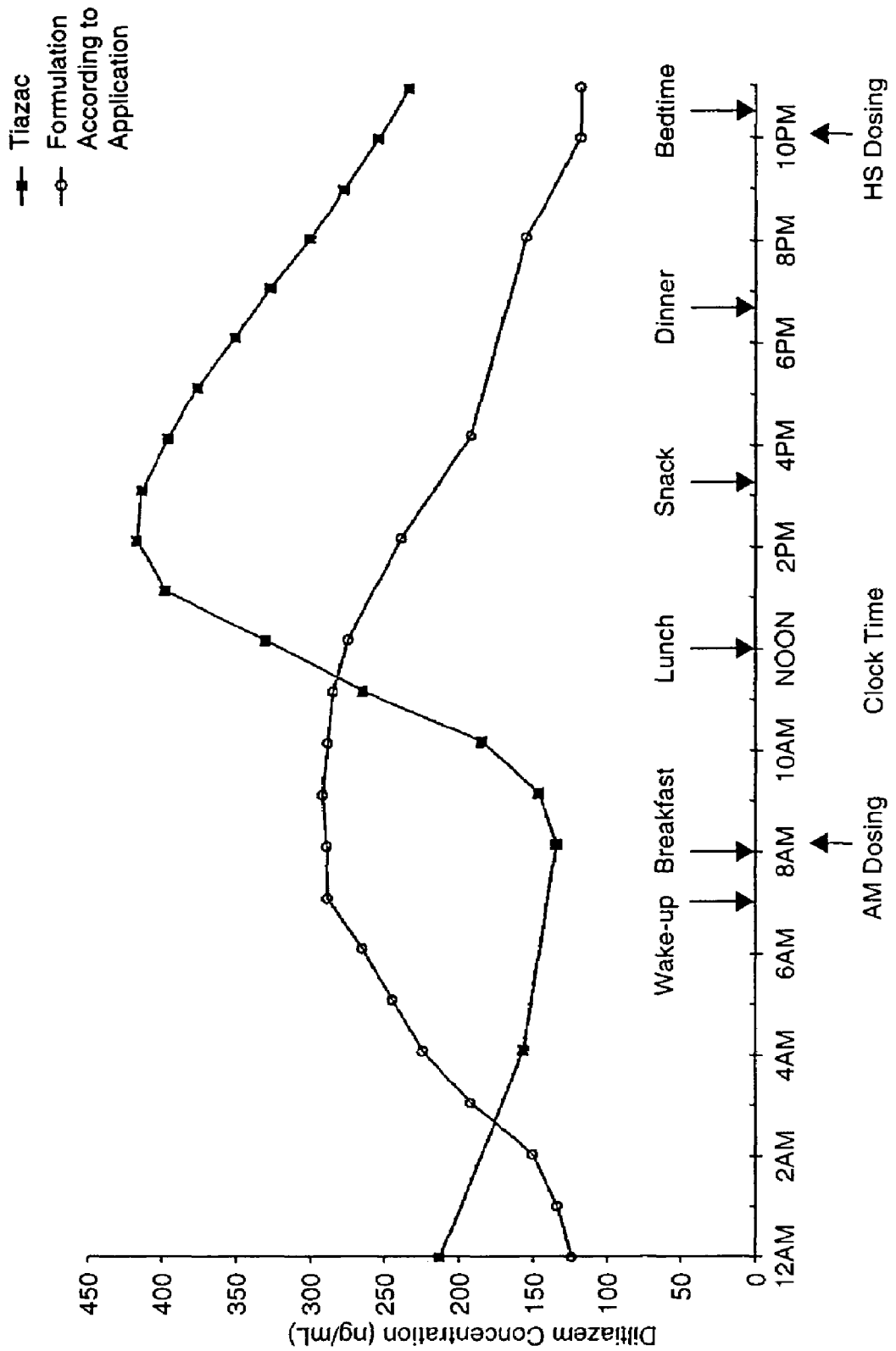
FIG. 8: is a graphic comparison of the blood level concentrations of a preparation (240 mg) made according to an embodiment of the invention and Tiazac (240 mg), a 24-hour oral sustained-release dosage form of Diltiazem.

The same is true with FIG. 8. Tiazac given in the morning, does not provide the protection. Further, peak plasma concentrations for Tiazac are achieved after about 7 hours after dose administration.

A 3-way single-dose study was undertaken using the same formulation (420 mg capsule) administered in the P.M. (10:00 P.M.) without food, and in the A.M. dosing with and without food.

3-Way Single-Dose Study

A: Formulation According to Embodiment of Invention—Fasting (AM Dosing)

B: Formulation According to Embodiment of Invention—Fed (AM Dosing)

C: Formulation According to Embodiment of Invention—(PM Dosing)

N=29

Figure 9:
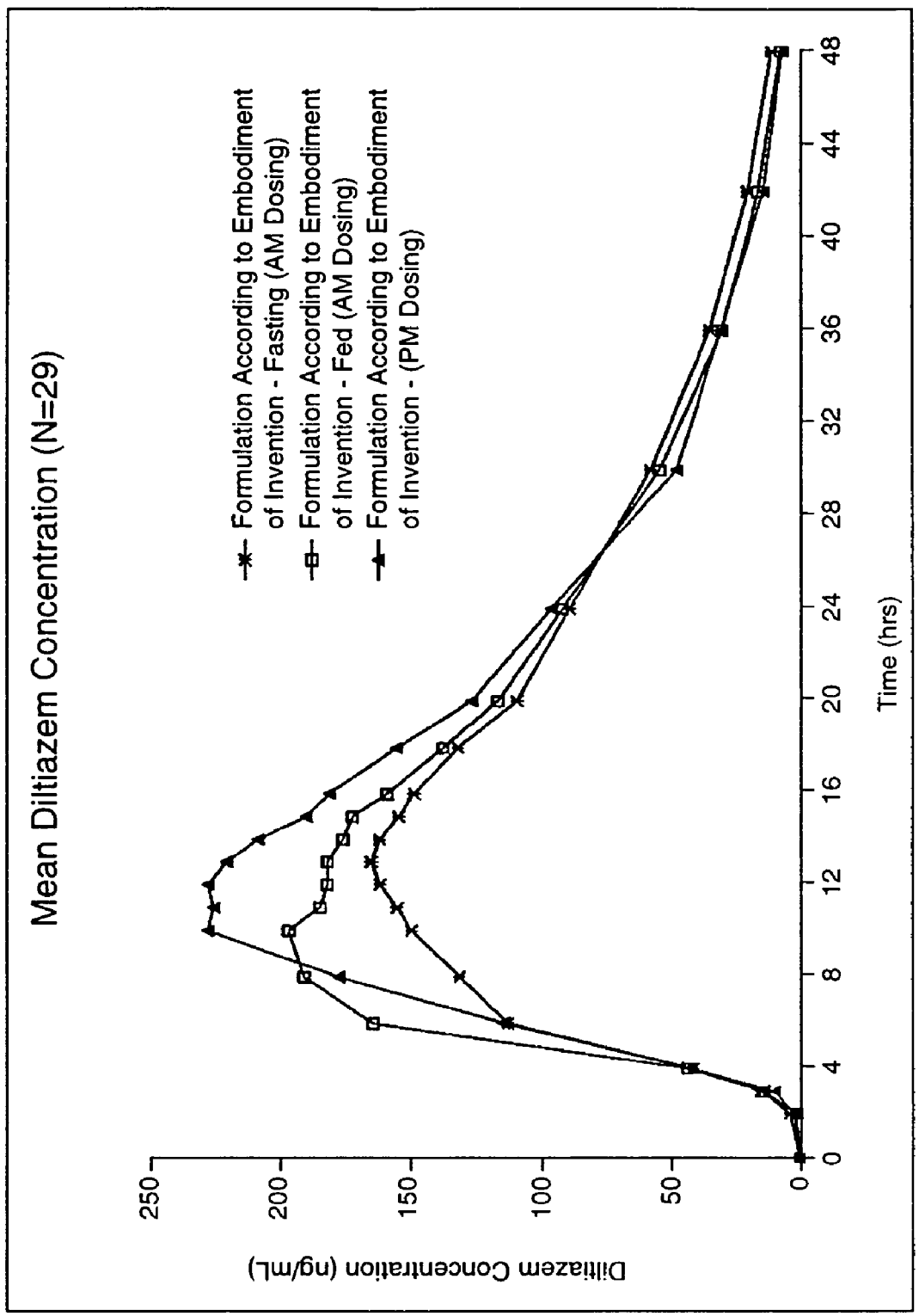
FIG. 9: illustrates graphically the Mean Diltiazem Concentration when administration of the same dosage form, is given in the P.M., in the A.M. with food and in the A.M. with fasting (without food) by 29 persons.

The results illustrated in FIG. 9A and FIG. 9B were found whose mean were graphically illustrated in FIG. 9.

A 2-way single-dose fasting study was undertaken using the same formulation (420 mg capsule) administered in the following manners—capsule intact and capsule opened and sprinkled on applesauce and ingested.

2-Way Single Dose Fasting Study

A: Formulation According to Embodiment of Inventions—Open Capsule Sprinkled on Applesauce B: Formulation According to Embodiment of Inventions—Capsule Intact

N=30 (FINAL DATA)

Figure 10:
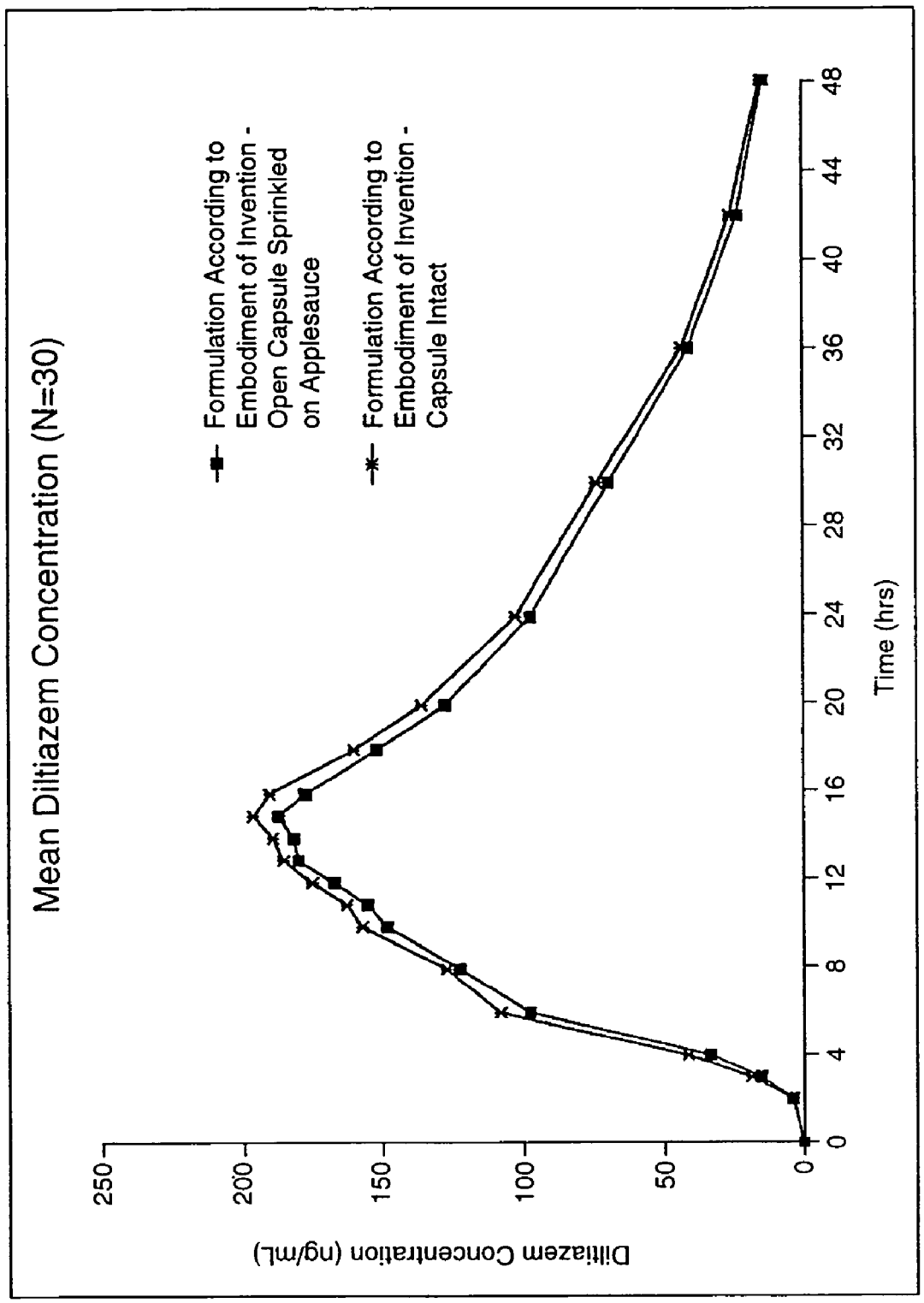
FIG. 10: illustrates graphically the Mean Diltiazem Concentration when the dosage form is an open capsule sprinkled on applesauce and swallowed and the dosage form is swallowed intact by 30 persons.

The results illustrated in FIGS. 10A, 10B and 10C were found whose mean were graphically illustrated in FIG. 10.

The preparations according to embodiments may also be made as tablets. The tablets may be made as compressed tablets in the desired strengths (for example 120 mg–540 mg or more Diltiazem) incorporating the microgranules. The tablets may even be scored to permit division into smaller doses.

Tablets may be made as follows using the microgranules or pellets, wax placebo beads and hydrogenated vegetable oil, sodium starch glycolate and silicone dioxide as follows:

The microgranules of Diltiazem may be the following:
Magnesium Stearate
Talc
Titanium Dioxide
Hydroxypropylmethyl-Cellulose 2910
Polysorbate 80
Simethicone Emulsion
Eudragit NE30D
Diltiazem Hydrochloride
Microcrystalline Cellulose
Povidone K30
Sucrose Stearate
Purified Water The wax placebo beads may be the following:
Microcrystalline Wax NF
Pregelatinized Starch
Sodium Starch Glycolate
Titanium Dioxide
Carbon Dioxide The microgranules, wax placebo beads, hydrogenated vegetable oil, sodium starch glycolate and silicone dioxide may be combined and compressed into the desired strengths of tablets, for example 240 mg, 300 mg and 360 mg tablets. Briefly, to form the microgranules, Diltiazem HCl, Microcrystalline Cellulose, Povidone 30, Sucrose Stearate may be mixed to form a "dry blend". A 1 kg portion of the dry blend may be removed and stored in a separate labeled container as the Dusting Powder, for use in subsequent manufacturing steps (if desired). Following the removal of the Dusting Powder, Purified Water is added to the dry blend and mixed to create a plastic mass. The plastic mass is extruded through a 1.0 mm screen to form a spaghetti like extrudate. This extrudate is then spheronized into beads. During the spheronization process Dusting Powder is added to dry the beads and provide them with a smooth aspect (if required). The addition of Dusting Powder also prevents the newly spheronized beads from sticking together. The spheronized beads are tray dried for 12–16 hours and sieved to select beads that are larger than 0.7 mm and smaller than 1.4 mm in diameter.

The beads are loaded into a preheated (40–45° C.) fluid bed Aerocoater. Coating suspension is applied at an amount of 10% by spray coating. The resulting Diltiazem Microgranules (coated beads) are dried for between 10–12 hours and the dried coated beads are sieved to select coated beads that are larger than 0.7 mm and smaller than 1.7 mm in diameter.

For the manufacture of the placebo wax beads, Microcrystalline Wax, Pregelatinized Maize Starch, Sodium Starch Glycolate and Titanium Dioxide are mixed in a high shear mixer and heated to 64° C. (jacket temperature 70° C.). The resulting melt is cooled by the addition of liquid $CO_2$ to form the solid starters of the pellets. The pellet starters are mixed and the size is increased by the gradual turning of the impeller for a fixed timeperiod (mixing time is directly related to the impeller speed and the time to reach a temperature of 57±2° C.). The resulting beads are sieved to select beads larger than 0.7 mm and smaller than 1.4 mm in diameter.

For manufacturing the Diltiazem chronotherapeutic tablets, the placebo wax beads and the microgranules of Diltiazem are blended at a ratio of about 2:3 (placebo wax beads:microgranules of Diltiazem) with Hydrogenated Vegetable Oil (lubricant), Sodium Starch Glycolate (disintegrant) and Silicone Dioxide (lubricant) added. The blend is tableted under low pressure (approximately 6–8 Sc) to form the compressed Diltiazem Tablets.

In the compressed tablets, the placebo wax beads serve to absorb the shock placed on the microgranules of Diltiazem during the tableting process. By doing so the integrity of the microgranules remains in tact and the release rate of the diltiazem is not affected.

As many changes can be made to the embodiments of the invention without departing from the scope thereof, it is intended that all material contained herein be determined as illustrative of the invention and not in a limiting sense.

The invention claimed is:

1. An orally administrable controlled-release composition comprising a pharmaceutically acceptable form of diltiazem selected from the group consisting of diltiazem and the pharmaceutically acceptable salts thereof, suitable for evening dosing every 24 hours, the dosage comprising at least one bead comprising a core and at least one coating, the at least one bead being formulated in an oral dosage form containing from about 120 mg to about 540 mg of the form of diltiazem, the diltiazem in the core of each bead associated with excipients, the at least one coating covering the core comprising an amount of a water swellable and diffusible coating which permits hydration of the core by gastrointestinal fluids, the water swellable and diffusible coating comprising the following constituents:
  (i) an amount of at least one hydrophilic polymer which is selected from the group consisting of hydroxypropylmethylcellulose, hydroxyethylcellulose, and hydroxypropylcellulose, and/or an amount of at least one lubricant which is selected from the group consisting of talc, and magnesium stearate; and
  (ii) an amount at least one water-, acid- or base-insoluble neutral acrylic polymer, wherein said constituents (i) and (ii) which comprise said coating, the ratios thereof, and the amount of said coating are formulated such that said orally administrable composition:
  A) in vitro exhibits the following in vitro release characteristics;
  (i) releases the diltiazem or a pharmaceutically acceptable salt thereof into an aqueous medium at the following rates when measured using the method of United States Pharmacopoeia No. XXIII at 100 rpm in 900 ml of water:
    (a) between about 1% and about 15% after about 2 hours;
    (b) between about 7% and about 35% after about 4 hours;
    (c) between about 30% and about 58% after about 8 hours;
    (d) between about 55% and about 80% after about 14 hours;
    (e) in excess of about 75% after about 24 hours; and/or
  (ii) releases the diltiazem or pharmaceutically acceptable salt thereof into a buffered medium having a pH between about 5.5 and about 6.5, at the following rates measured using the method of United States Pharmacopoeia No. XXIII at 100 rpm in 900 ml of the buffered medium:
    (a) between about 1% and about 25% after about 2 hours;
    (b) between about 7% and about 45% after about 4 hours;
    (c) between about 30% and about 68% after about 8 hours;
    (d) in excess of about 75% after about 24 hours; and
  further wherein said orally administrable composition having said in vitro release characteristics results in a composition that:
  B) when orally given to humans exhibit the following properties:
    (i) a higher bioavailability when given at night compared to when given in the morning without food according to FDA guidelines or criteria and
    (ii) bioequivalence when given in the morning with or without food according to the same FDA guidelines or criteria; and
    (iii) provides a Cmax of diltiazem in the blood at between about 10 hours and 15 hours after administration.

2. The controlled release preparation of claim 1 wherein said neutral acrylic polymer is a neutral copolymer of acrylic acid ethyl ester and acrylic acid methyl ester.

3. The controlled-release preparation of claim 1 in which the form of diltiazem is adapted to be control released after administration of the preparation over a period of time and is more preferably adapted to release the diltiazem
  (i) into an aqueous medium at the following rates measured using the method of United States Pharmacopoeia No. XXIII at 100 rpm in 900 ml of water:
    (a) between about 4% and about 8% after about 2 hours;
    (b) between about 16% and about 21% after about 4 hours;
    (c) between about 44% and about 52% after about 8 hours;
    (d) between about 69% and about 76% after about 14 hours; and
    (e) and in excess of about 85% after about 24 hours;
  and/or (ii) into a buffered medium having a pH about 5.8 at the following rates measured using the method of United States Pharmacopoeia No. XXIII at 100 rpm in 900 ml of the buffered medium:
    (a) between about 4% and about 15% after about 2 hours;
    (b) between about 16% and about 30% after about 4 hours;
    (c) between about 44% and about 62% after about 8 hours;
    (d) in excess of about 80% after about 24 hours.

4. The preparation of claim 1 wherein the Cmax of diltiazem in the blood is obtained between about 11–about 13 hours after administration of the preparation.

5. The preparation of claim 1, 2, 3 or 4 wherein the form of diltiazem is Diltiazem HCl.

6. The preparation of claim 4 wherein the preparation is a diffusion controlled preparation.

7. The preparation of claim 3 wherein the preparation releases the diltiazem at a rate of less than about 15% of the total amount of active per hour during dissolution.

8. The preparation of claim 7 in capsule form.

9. The preparation of claim 7 in tablet form.

10. The preparation of claim 7 wherein the preparation comprises a plurality of microgranules, each microgranule comprising a central core containing the form of diltiazem coated with a microporous membrane and the central core comprises diltiazem or pharmaceutically acceptable salt thereof associated with a wetting agent.

11. The preparation of claim 10 wherein the diltiazem is mixed (in whole or in part) with the wetting agent.

12. The preparation of claim 11 wherein the wetting agent assists to maintain the solubility of the diltiazem in each microgranule, ensuring that the solubility of the diltiazem is unaffected by the pH of the gastrointestinal tract or other adverse conditions which the composition will meet therein.

13. The preparation of claim 12 wherein the membrane comprises a water-dispersible or water-soluble polymer and a water-, acid- and base-insoluble polymer of a neutral acrylic polymer of acrylic acid ethyl ester and acrylic acid methyl ester which hydrates the preparation.

14. The preparation of claim 10 wherein the preparation comprises a mixture of the diltiazem and/or pharmaceutically acceptable salt with the wetting agent and the membrane comprises a water-dispersible or water-soluble polymer and a water-, acid- and base-insoluble polymer of a neutral acrylic polymer of acrylic acid ethyl ester and acrylic acid methyl ester which hydrates the preparation.

15. The preparation of claim 14 wherein the membrane comprises a neutral acrylic polymer of acrylic acid ethyl ester and acrylic acid methyl ester and hydroxypropylmethylcellulose.

16. The preparation of claim 15 wherein the membrane hydrates the core within a membrane which when put in gastrointestinal fluid causes the membrane to swell while fluid penetrates and hydrates the microgranule, and dissolves the diltiazem and wetting agent and benefits from a concentration gradient through the membrane (high concentration inside and low concentration outside).

17. The preparation of claim 11 wherein the diltiazem is mixed with the wetting agent and the membrane comprises an acrylic membrane and plasticizer combined to form the membrane thereby providing a mechanism of release from this membrane which "washes" the diltiazem through pores created when the plasticizer incorporated in the membrane, is released in gastrointestinal fluid.

18. The preparation of claim 7 wherein the preparation comprises a plurality of microgranules comprising a central core containing the form of diltiazem coated with a microporous membrane and the central core comprises diltiazem or a pharmaceutically acceptable salt thereof associated with any suitable dissolution agent (other than a wetting agent) to assist in the release of the diltiazem from the preparation.

19. The preparation of claim 18 wherein the dissolution agent is an organic acid comprising adipic acid, ascorbic acid, citric acid, fumaric acid, malic acid, succinic acid or tartaric acid which permits the diltiazem to dissolve in gastrointestinal fluids even when the microgranules pass into the regions of the gastrointestinal tract of the intestine at which pH diltiazem is much less soluble.

20. A method of treatment of a patient's hypertension and/or angina comprising the administration of the preparation of diltiazem of claim 1 to the patient in the evening for effective treatment of the patient's hypertension and/or angina the next morning, the method comprising administering to a patient in need thereof the preparation in the evening.

21. A method of treatment of a patient's hypertension and/or angina comprising the administration of the preparation of diltiazem of claim 2 to the patient in the evening for effective treatment of the patient's hypertension and/or angina the next morning.

22. A method of treatment of a patient's hypertension and/or angina comprising the administration of the preparation of diltiazem of claim 3 to the patient in the evening for effective treatment of the patient's hypertension and/or angina the next morning.

23. A method of treatment of a patient's hypertension and/or angina comprising the administration of the preparation of diltiazem of claim 4 to the patient in the evening for effective treatment of the patient's hypertension and/or angina the next morning.

24. A method of treatment of a patient's hypertension and/or angina comprising the administration of the preparation of diltiazem of claim 5 to the patient in the evening for effective treatment of the patient's hypertension and/or angina the next morning.

25. A method of treatment of a patient's hypertension and/or angina comprising the administration of the preparation of diltiazem of claim 6 to the patient in the evening for effective treatment of the patient's hypertension and/or angina the next morning.

26. A method of treatment of a patient's hypertension and/or angina comprising the administration of the preparation of diltiazem of claim 7 to the patient in the evening for effective treatment of the patient's hypertension and/or angina the next morning.

27. A method of treatment of a patient's hypertension and/or angina comprising the administration of the preparation of diltiazem of claim 8 to the patient in the evening for effective treatment of the patient's hypertension and/or angina the next morning.

28. A method of treatment of a patient's hypertension and/or angina comprising the administration of the preparation of diltiazem of claim 9 to the patient in the evening for effective treatment of the patient's hypertension and/or angina the next morning.

29. A method of treatment of a patient's hypertension and/or angina comprising the administration of the preparation of diltiazem of claim 10 to the patient in the evening for effective treatment of the patient's hypertension and/or angina the next morning.

30. A method of treatment of a patient's hypertension and/or angina comprising the administration of the preparation of diltiazem of claim 11 to the patient in the evening for effective treatment of the patient's hypertension and/or angina the next morning.

31. A method of treatment of a patient's hypertension and/or angina comprising the administration of the preparation of diltiazem of claim 12 to the patient in the evening for effective treatment of the patient's hypertension and/or angina the next morning.

32. A method of treatment of a patient's hypertension and/or angina comprising the administration of the preparation of diltiazem of claim 13 to the patient in the evening for effective treatment of the patient's hypertension and/or angina the next morning.

33. A method of treatment of a patient's hypertension and/or angina comprising the administration of the preparation of diltiazem of claim 14 to the patient in the evening for effective treatment of the patient's hypertension and/or angina the next morning.

34. A method of treatment of a patient's hypertension and/or angina comprising the administration of the preparation of diltiazem of claim 15 to the patient in the evening for effective treatment of the patient's hypertension and/or angina the next morning.

35. A method of treatment of a patient's hypertension and/or angina comprising the administration of the preparation of diltiazem of claim 16 to the patient in the evening for effective treatment of the patient's hypertension and/or angina the next morning.

36. A method of treatment of a patient's hypertension and/or angina comprising the administration of the preparation of diltiazem of claim 17 to the patient in the evening for effective treatment of the patient's hypertension and/or angina the next morning.

37. A method of treatment of a patient's hypertension and/or angina comprising the administration of the preparation of diltiazem of claim 18 to the patient in the evening for effective treatment of the patient's hypertension and/or angina the next morning.

38. A method of treatment of a patient's hypertension and/or angina comprising the administration of the preparation of diltiazem of claim 19 to the patient in the evening for effective treatment of the patient's hypertension and/or angina the next morning.

39. The preparation of claim 1 wherein the preparation contains 120 mg of diltiazem.

40. The preparation of claim 1 wherein the preparation contains 180 mg of diltiazem.

41. The preparation of claim 1 wherein the preparation contains 240 mg of diltiazem.

42. The preparation of claim 1 wherein the preparation contains 300 mg of diltiazem.

43. The preparation of claim 1 wherein the preparation contains 360 mg of diltiazem.

44. The preparation of claim 1 wherein the preparation contains 420 mg of diltiazem.

45. A method of treatment of a patient's hypertension and/or angina comprising the administration of the preparation of diltiazem of claim 39, 40, 41, 42, 43 or 44 to the patient in the evening for effective treatment of the patient's hypertension and/or angina the next morning.

46. The preparation of claim 15 wherein the wetting agent is selected from:
sugars;
saccharose, mannitol, sorbitol;
lecithins;
$C_{12}$ to $C_{20}$ fatty acid esters of saccarose;
xylose esters or xylites;
polyoxyethylenic glycerrides;
esters of fatty acids and polyoxyethylene;
sorbitan fatty acid ester;
polyglycides-glycerides and polyglycides-alcohols ester; and metal salts.

47. The preparation of claim 10 wherein the wetting agent is in association with the diltiazem in the microgranule and not mixed therewith, the membrane comprises a water-soluble or water dispersible polymer or copolymer selected from the group consisting of hydroxypropylmethylcellulose and a water-, acid- and base-insoluble polymer which is a neutral copolymer of acrylic acid ethyl ester and acrylic acid methyl ester which enables the bead to be hydrated by the introduction of gastrointestinal fluids into the core hydrating the core and therefore mixing the diltiazem and the wetting agent.

48. A method of treatment of a patient's hypertension and/or angina comprising the administration of the preparation of diltiazem of claim 46 to the patient in the evening for effective treatment of the patient's hypertension and/or angina the next morning.

49. A method of treatment of a patient's hypertension and/or angina comprising the administration of the preparation of diltiazem of claim 47 to the patient in the evening for effective treatment of the patient's hypertension and/or angina the next morning.

50. A controlled-release preparation of pharmaceutically acceptable form of diltiazem according to claim 1 which comprises the following constituents:

|  |  | % W/W |
|---|---|---|
| (i) in the core: | | |
| (a) | Diltiazem hydrochloride | 69–73 |
| (b) | Microcrystalline cellulose | 8–9.5 |
| (c) | (Polyvinyl Pyrrolidone) | 1–2 |
| (d) | Sucrose stearate | 7–8 |
| (ii) in the membrane: | | |
| (e) | Magnesium stearate NF | 0.5–2.5 |
| (f) | Talc USP | 0.5–5.0 |
| (g) | Titanium dioxide. (USP) | 0.15–0.3 |
| (h) | Hydroxypropylmethylcellulose 2910 | 0.3–0.6 |
| (i) | (Polyoxyethylene Sorbitan Monooleate) | 0.01–0.025 |
| (j) | Simethicone C emulsion USP. (dry of 30%) | 0.01–0.015 |
| (k) | a neutral acrylic polymer of acrylic acid ethyl ester and acrylic acid methyl ester (dry of 30%) | 7–11 |
|  | Purified water USP | 0 (used for mixing). |

51. A method of treatment of a patient's hypertension and/or angina comprising the administration of the preparation of diltiazem of claim 50 to the patient in the evening for effective treatment of the patient's hypertension and/or angina the next morning.

52. The preparation of claim 10 in which the core and membrane comprise:
(i) in the core,
(a) between about 50% and about 85% (% w/w of the total preparation) of diltiazem or pharmaceutically acceptable salt thereof; and
(b) between about 2% and about 25% wetting agent (% w/w of the total preparation);
together with suitable adjuvants; and
(ii) in the membrane,
(c) between about 0.1% and about 50% of the total preparation of lubricant selected from the group consisting of talc, and magnesium stearate;
(d) between about 0.1% and about 2% of the total preparation of water-soluble and/or water-dispersible polymer selected from the group consisting of hydroxypropylmethylcellulose, hydroxyethyl-cellulose, hydroxypropylcellulose, and any combination thereof; and
(e) between about 5% and about 20% (% w/w of the preparation) of a neutral copolymer of acrylic acid ethyl ester and acrylic acid methyl ester, together with suitable adjuvants.

53. A method of treatment of a patient's hypertension and/or angina comprising the administration of the preparation of diltiazem of claim 52 to the patient in the evening for effective treatment of the patient's hypertension and/or angina the next morning.

54. The preparation of claim 10 in which the core and membrane comprise:
(i) in the core,
(a) between about 69% and about 73% (% w/w of the total preparation) of diltiazem or pharmaceutically acceptable salt thereof; and (b) between about 7% and about 8% wetting agent (% w/w of the total preparation);
together with suitable adjuvants; and
(ii) in the membrane,
  (c) between about 0.1% and about 50% of the total preparation of lubricant selected from the group consisting of talc, and magnesium stearate;
  (d) between about 0.3% and about 0.6% of the total preparation of water-soluble and/or water-dispersible polymer selected from the group consisting of hydroxypropylmethylcellulose, hydroxyethylcellulose, hydroxypropylcellulose, and any combination thereof; and
  (e) between about 7% and about 11% (% w/w of the preparation) of a neutral copolymer of acrylic acid ethyl ester and acrylic acid methyl ester, together with suitable adjuvants.

55. A method of treatment of a patient's hypertension and/or angina comprising the administration of the preparation of diltiazem of claim 54 to the patient in the evening for effective treatment of the patient's hypertension and/or angina the next morning.

56. The preparation of claim 10 wherein the preparation is a tablet and the tablet comprises microgranules in association with wax placebo beads which wax placebo beads serve to absorb the shock placed on the microgranules of diltiazem during the tablet process, together with suitable excipients and adjuvants.

57. A method of treatment of a patient's hypertension and/or angina comprising the administration of the preparation of diltiazem of claim 56 to the patient in the evening for effective treatment of the patient's hypertension and/or angina the next morning.

58. The controlled-release preparation of claim 2 in which the diltiazem is adapted to be control released after administration of the preparation over a period of time wherein the preparation comprises a plurality of microgranules, each microgranule comprising a central core containing the form of diltiazem coated with a microporous membrane and the central core comprises diltiazem or pharmaceutically acceptable salt thereof associated with a wetting agent in which the core and membrane comprise:
(i) in the core,
  (a) between about 50% and about 85% (% w/w of the total preparation) of diltiazem or pharmaceutically acceptable salt thereof; and
  (b) between about 2% and about 25% wetting agent (% w/w of the total preparation);
together with suitable adjuvants; and
(ii) in the membrane,
  (c) between 0.1% and about 50% of the total preparation of lubricant selected from the group consisting of talc, and magnesium stearate;
  (d) between about 0.1% and about 2% of the total preparation of water-soluble and/or water-dispersible polymer selected from the group consisting of hydroxypropylmethylcellulose, hydroxyethylcellulose, hydroxypropylcellulose, and any combination thereof; and
  (e) between about 5% and about 20% (% w/w of the preparation) of a neutral copolymer of acrylic acid ethyl ester and acrylic acid methyl ester, together with suitable adjuvants.

59. The preparation of claim 58 wherein the microgranules are in capsule form.

60. The preparation of claim 58 wherein the microgranules are in tablet form.

61. The preparation of claim 58 wherein the core and membrane comprise:
(i) in the core,
  (a) between about 69% and about 73% (% w/w of the total preparation) of diltiazem or pharmaceutically acceptable salt thereof; and
  (b) between about 7% and about 8% wetting agent (% w/w of the total preparation);
together with suitable adjuvants; and
(ii) in the membrane,
  (c) between about 0.1% and about 50% of the total preparation of lubricant selected from the group consisting of talc, and magnesium stearate;
  (d) between about 0.3% and about 0.6% of the total preparation of water-soluble and/or water-dispersible polymer selected from the group consisting of hydroxypropylmethylcellulose, hydroxyethylcellulose, hydroxypropylcellulose, and any combination thereof; and
  (e) between about 7% and about 11% (% w/w of the preparation) of a neutral copolymer of acrylic acid ethyl ester and acrylic acid methyl ester, together with suitable adjuvants.

62. A controlled-release preparation of pharmaceutically acceptable form of diltiazem according to claim 1, which preparation comprises a plurality of microgranules, each microgranule comprising a central core containing the form of diltiazem coated with a microporous membrane and the central core comprises diltiazem or pharmaceutically acceptable salt thereof associated with a wetting agent in which the core and membrane comprise:

|  | % W/W |
|---|---|
| (i) in the core: | |
| (a) Diltiazem hydrochloride | 69–73 |
| (b) Microcrystalline cellulose | 8–9.5 |
| (c) (Polyvinyl Pyrrolidone) | 1–2 |
| (d) Sucrose stearate | 7–8 |
| (ii) in the membrane: | |
| (e) Magnesium stearate NF | 0.5–2.5 |
| (f) Talc USP | 0.5–5.0 |
| (g) Titanium dioxide. (USP) | 0.15–0.3 |
| (h) Hydroxypropylmethylcellulose 2910 | 0.3–0.6 |
| (i) (Polyoxyethylene Sorbitan Monooleate) | 0.01–0.025 |
| (j) Simethicone C emulsion USP. (dry of 30%) | 0.01–0.015 |
| (k) a neutral acrylic polymer of acrylic acid ethyl ester and acrylic acid methyl ester (dry of 30%) | 7–11 |
| Purified water USP | 0 (used for mixing). |

63. The preparation of claim 58 wherein the preparation is a tablet and the tablet comprises microgranules in association with wax placebo beads which wax placebo beads serve to absorb the shock placed on the microgranules of diltiazem during the tablet process, together with suitable excipients and adjuvants.

64. A method of treatment of a patient's hypertension and/or angina comprising the administration of the preparation of diltiazem of claim 58 to the patient in the evening for effective treatment of the patient's hypertension and/or angina the next morning.

65. A controlled-release preparation of pharmaceutically acceptable form of diltiazem according to claim 1, wherein the preparation comprises a plurality of microgranules, each microgranule comprising a central core containing the form of diltiazem coated with a microporous membrane and the central core comprises diltiazem or pharmaceutically acceptable salt thereof associated with a wetting agent, wherein the wetting agent is selected from:
sugars;
saccharose, mannitol, sorbitol;
lecithins;
$C_{12}$ to $C_{20}$ fatty acid esters of saccharose;
xylose esters or xylites;
polyoxyethylenic glycerrides;
esters of fatty acids and polyoxyethylene;
sorbitan fatty acid esters;
polyglycides-glycerides and polyglycides-alcohols ester; and metal salts.

66. A method of treatment of a patient's hypertension and/or angina comprising the administration of the preparation of diltiazem of claim 65 to the patient in the evening for effective treatment of the patient's hypertension and/or angina the next morning.

67. A method of treatment of a patient's hypertension and/or angina comprising the administration of the preparation of diltiazem of claim 63 to the patient in the evening for effective treatment of the patient's hypertension and/or angina the next morning.

68. A controlled-release preparation of pharmaceutically acceptable form of diltiazem according to claim 1 wherein the preparation comprises a plurality of microgranules, each microgranule comprising a central core containing the form of diltiazem coated with a microporous membrane and the central core comprises diltiazem or pharmaceutically acceptable salt thereof associated with a wetting agent, in which the core and membrane comprise:

|  |  | % W/W |
|---|---|---|
| (i) in the core: | | |
| (a) | Diltiazem hydrochloride | 69–73 |
| (b) | Microcrystalline cellulose | 8–9.5 |
| (c) | (Polyvinyl Pyrrolidone) | 1–2 |
| (d) | Sucrose stearate | 7–8 |
| (ii) in the membrane: | | |
| (e) | Magnesium stearate NF | 0.5–2.5 |
| (f) | Talc USP | 0.5–5.0 |
| (g) | Titanium dioxide. (USP) | 0.15–0.3 |
| (h) | Hydroxypropylmethylcellulose 2910 | 0.3–0.6 |
| (i) | (Polyoxyethylene Sorbitan Monooleate) | 0.01–0.025 |
| (l) | Simethicone C emulsion USP. (dry of 30%) | 0.01–0.015 |
| (k) | neutral acrylic polymer of acrylic acid ethyl ester and acrylic acid methyl ester (dry of 30%) | 7–11 |
|  | Purified water USP | 0 (used for mixing). |

69. A method of treatment of a patient's hypertension and/or angina comprising the administration of the preparation of diltiazem of claim 66 to the patient in the evening for effective treatment of the patient's hypertension and/or angina the next morning.

70. A controlled-release preparation of pharmaceutically acceptable form of diltiazem according to claim 3, wherein the preparation comprises a plurality of microgranules, each microgranule comprising a central core containing the form of diltiazem coated with a microporous membrane and the central core comprises diltiazem or pharmaceutically acceptable salt thereof associated with a wetting agent, in which the core and membrane comprise:
(i) in the core,
(a) between about 50% and about 85% (% w/w of the total preparation) of diltiazem or pharmaceutically acceptable salt thereof; and
(b) between about 2% and about 25% wetting agent (% w/w of the total preparation);
together with suitable adjuvants; and
(ii) in the membrane,
(c) between about 0.1% and about 50% of the total preparation of lubricant selected from the group consisting of talc, and magnesium stearate;
(d) between about 0.1% and about 2% of the total preparation of water-soluble and/or water-dispersible polymer selected from the group consisting of hydroxypropylmethylcellulose, hydroxyethylcellulose, hydroxypropylcellulose, and any combination thereof; and
(e) between about 5% and about 20% (% w/w of the preparation) of a neutral copolymer of acrylic acid ethyl ester and acrylic acid methyl ester, together with suitable adjuvants which permits hydration of the core by gastrointestinal fluids.

71. A method of treatment of a patient's hypertension and/or angina comprising the administration of the preparation of diltiazem of claim 70 to the patient in the evening for effective treatment of the patient's hypertension and/or angina the next morning.

72. A controlled-release preparation of pharmaceutically acceptable form of diltiazem according to claim 3, wherein the preparation comprises a plurality of microgranules, each microgranule comprising a central core containing the form of diltiazem coated with a microporous membrane and the central core comprises diltiazem or pharmaceutically acceptable salt thereof associated with a wetting agent, in which the core and membrane comprise:
(i) in the core,
(a) between about 69% and about 73% (% w/w of the total preparation) of diltiazem or pharmaceutically acceptable salt thereof; and
(b) between about 7% and about 8% wetting agent (% w/w of the total preparation);
together with suitable adjuvants; and
(ii) in the membrane,
(c) between about 0.1% and about 50% of the total preparation of lubricant selected from the group consisting of talc, and magnesium stearate;
(d) between about 0.3% and about 0.6% of the total preparation of water-soluble and/or water-dispersible polymer selected from the group consisting of hydroxypropylmethylcellulose, hydroxyethylcellulose, hydroxypropylcellulose, and any combination thereof; and
(e) between about 7% and about 11% (% w/w of the preparation) of a neutral copolymer of acrylic acid ethyl ester and acrylic acid methyl ester, together with suitable adjuvants which permits hydration of the core by gastrointestinal fluids.

73. A method of treatment of a patient's hypertension and/or angina comprising the administration of the preparation of diltiazem of claim 72 to the patient in the evening for effective treatment of the patient's hypertension and/or angina the next morning.

74. A controlled-release preparation of pharmaceutically acceptable form of diltiazem according to claim 1 wherein the preparation comprises a plurality of microgranules, each microgranule comprising a central core containing the form of diltiazem coated with a microporous membrane and the central core comprises diltiazem or pharmaceutically acceptable salt thereof associated with a wetting agent in which the core and membrane comprise:
- (i) in the core,
  - (a) between about 50% and about 85% (% w/w of the total preparation) of diltiazem or pharmaceutically acceptable salt thereof; and
  - (b) between about 2% and about 25% wetting agent (% w/w of the total preparation);
  together with suitable adjuvants; and
- (ii) in the membrane,
  - (c) between about 0.1% and about 50% of the total preparation of lubricant selected from the group consisting of talc, and magnesium stearate;
  - (d) between about 0.1% and about 2% of the total preparation of water-soluble and/or water-dispersible polymer selected from the group consisting of hydroxypropylmethylcellulose, hydroxyethylcellulose, hydroxypropylcellulose, and any combination thereof; and
  - (e) between about 5% and about 20% (% w/w of the preparation) of a neutral copolymer of acrylic acid ethyl ester and acrylic acid methyl ester, together with suitable adjuvants which permits hydration of the core by gastrointestinal fluids.

75. The preparation of claim 74 wherein the microgranules are in capsule form.

76. The preparation of claim 74 wherein the microgranules are in tablet form.

77. The preparation of claim 74, 75 or 76 wherein the core and membrane comprise:
- (i) in the core,
  - (a) between about 69% and about 73% (% w/w of the total preparation) of diltiazem or pharmaceutically acceptable salt thereof; and
  - (b) between about 7% and about 8% wetting agent (% w/w of the total preparation);
  together with suitable adjuvants; and
- (ii) in the membrane,
  - (c) between about 0.1% and about 50% of the total preparation of lubricant selected from the group consisting of talc, and magnesium stearate;
  - (d) between about 0.3% and about 0.6% of the total preparation of water-soluble and/or water-dispersible polymer selected from the group consisting of hydroxypropylmethylcellulose, hydroxyethyl-cellulose, hydroxypropylcellulose, and any combination thereof; and
  - (e) between about 7% and about 11% (% w/w of the preparation) of a neutral copolymer of acrylic acid ethyl ester and acrylic acid methyl ester, together with suitable adjuvants.

78. The preparation of claim 74, 75 or 76 wherein the core and membrane comprise:

|  | % W/W |
| --- | --- |
| (i) in the core: | |
| (a) Diltiazem hydrochloride | 69–73 |
| (b) Microcrystalline cellulose | 8–9.5 |
| (c) (Polyvinyl Pyrrolidone) | 1–2 |
| (d) Sucrose stearate | 7–8 |
| (ii) in the membrane: | |
| (e) Magnesium stearate NF | 0.5–2.5 |
| (f) Talc USP | 0.5–5.0 |
| (g) Titanium dioxide. (USP) | 0.15–0.3 |
| (h) Hydroxypropylmethylcellulose 2910 | 0.3–0.6 |
| (i) (Polyoxyethylene Sorbitan Monooleate) | 0.01–0.025 |
| (j) Simethicone C emulsion USP. (dry of 30%) | 0.01–0.015 |
| (k) a neutral acrylic polymer of acrylic acid ethyl ester and acrylic acid methyl ester. (dry of 30%) | 7–11 |
| Purified water USP | 0 (used for mixing). |

79. The preparation of claim 74 or 76 wherein the preparation is a tablet and the tablet comprises microgranules in association with wax placebo beads which wax placebo beads serve to absorb the shock placed on the microgranules of diltiazem during the tablet process, together with suitable excipients and adjuvants.

80. A method of treatment of a patient's hypertension and/or angina comprising the administration of the preparation of diltiazem of claim 74, 75 or 76 to the patient in the evening for effective treatment of the patient's hypertension and/or angina the next morning.

81. The controlled release preparation of claim 1 wherein said neutral acrylic polymer is a neutral copolymer of acrylic acid ethyl ester and acrylic acid methyl ester.

82. The preparation of claim 70, 72 and 74 wherein the lubricant is selected from the group consisting of talc, and magnesium stearate.

83. A method of treatment of a patient's hypertension and/or angina comprising the administration of the preparation of diltiazem of claim 81 to the patient in the evening for effective treatment of the patient's hypertension and/or angina the next morning.

84. A method of treatment of a patient's hypertension and/or angina comprising the administration of the preparation of diltiazem of claim 82 to the patient in the evening for effective treatment of the patient's hypertension and/or angina the next morning.

85. The preparation of claim 1 in capsule form.

86. The preparation of claim 1 in tablet form.

87. The preparation of claim 2 in capsule form.

88. The preparation of claim 2 in tablet form.

* * * * *